United States Patent
Powell

(10) Patent No.: US 8,075,902 B2
(45) Date of Patent: *Dec. 13, 2011

(54) DIAGNOSIS AND TREATMENT OF CANCER RELATED TO HUMAN DORMANCY

(76) Inventor: Michael Powell, Sacramento, CA (US)

( * ) Notice: Subject to any disclaimer, the term of this patent is extended or adjusted under 35 U.S.C. 154(b) by 531 days.

This patent is subject to a terminal disclaimer.

(21) Appl. No.: 12/006,462

(22) Filed: Jan. 2, 2008

(65) Prior Publication Data

US 2008/0160007 A1     Jul. 3, 2008

Related U.S. Application Data

(60) Provisional application No. 60/878,343, filed on Jan. 3, 2007.

(51) Int. Cl.
*G01N 33/78* (2006.01)
*C07G 13/00* (2006.01)
*C07G 11/00* (2006.01)
*A01N 59/12* (2006.01)
*A61K 31/00* (2006.01)

(52) U.S. Cl. .................... 424/198.1; 424/667; 424/94.6; 514/343; 514/474; 536/8; 536/16.8; 436/500

(58) Field of Classification Search ................. 424/94.6, 424/198.1, 667; 436/500; 514/343, 474; 536/8, 16.8
See application file for complete search history.

(56) References Cited

U.S. PATENT DOCUMENTS

2003/0228628 A1 * 12/2003 Powell .......................... 435/7.1
* cited by examiner

*Primary Examiner* — Taeyoon Kim
(74) *Attorney, Agent, or Firm* — D. Benjamin Borson; Borson Law Group, PC

(57) ABSTRACT

New devices and methods for diagnosis and compositions and methods for treatment of cancers use combinations of antimicrobial agents and agents that can reverse dormancy and hibernation pathways. We unexpectedly found that surprisingly low doses of anti-hibernation compounds can substantially inhibit cancer cell growth in vitro and can successfully treat cancers, including metastatic cancer. We also unexpectedly found that antimicrobial agents and anti-HDS compounds together can increase the degree of inhibition of cancer cell growth in a synergistic fashion. We conclude that combination therapy with antimicrobial agents and anti-HDS compounds can be effective in treating human patients with cancer.

11 Claims, 2 Drawing Sheets

DIAGNOSIS AND TREATMENT OF CANCER RELATED TO HUMAN DORMANCY

PRIORITY CLAIM

This application claims priority to U.S. Provisional Patent Application No. 60/878,343, filed Jan. 3, 2007. This application is expressly incorporated herein in its entirety.

FIELD OF THE INVENTION

This invention relates to methods for treating cancer related to human dormancy syndrome (HDS). In particular, this invention relates to devices and methods for diagnosing HDS and to compositions and methods for treating cancer associated with HDS using combination therapy using antibiotics and anti-hibernation compounds.

BACKGROUND

Cancer is one of the most difficult types of diseases to treat. Cancers are known to be multifactoral, involving genetic predisposition, uncontrollable environmental factors and controllable factors, such as smoking, ingestion of carcinogens, exposure to environmental toxins and other factors. Morbidity and mortality exact a large human and economic cost from our society. Current therapies for cancer include chemotherapy using cytotoxic agents, antibodies against cancer cells, cessation of exposure to carcinogens and/or radiation therapy.

Although many cancers respond to these conventional therapies, many types of cancer are refractive to them. In many cases, such as cancer of the pancreatic head, once a diagnosis is made, the patient typically has a life expectancy of only several months.

Early diagnosis of cancer has been one of the more effective determinants of successful anti-cancer therapy. Many methods are used to detect cancer, including histological examination, detection of cancer markers in serum and other bodily fluids, physical examination, patient history, magnetic resonance imaging, positron emission tomography, x-ray, ultrasound and other methods.

Human Dormancy Syndrome (HDS), also termed "Human Hibernation Syndrome" is a newly recognized syndrome involving several interrelated biochemical and physiological processes that can result in a number of different recognized disorders (see U.S. Pat. No. 7,288,257, incorporated herein fully by reference). A common underlying theme of all disorders within HDS is development of resistance to stress, characterized by "shutting down" of one or more physiological processes. For example, the fetal environment, responses to cold temperatures, starvation and other types of situations can produce a biological response similar to hibernation of other mammalian and bird species.

One characteristic of certain disorders in HDS includes elevated reverse triiodothyronine ("rT3") to free triiodothyronine ("fT3") ratio and one or more symptoms (see U.S. Pat. No. 7,288,257, issued Oct. 30, 2007). Diagnosis of HDS was enabled by the recognition that the rT3/fT3 ratio of prior studies was inaccurate, in that subjects considered "normal," in fact, had a disorder as described in the above patent. The recognition of a lower level of rT3/fT3 in "true normal" subjects, and the diagnosis of HDS has led to improved treatment.

However, mechanisms of cancer formation and factors that contribute to cancer growth are not well known. There is general acceptance that certain cancers are associated with mutations in genes (oncogenes) that are present in human cells. Other types of cancers are known to be associated with certain viral infections.

SUMMARY OF THE INVENTION

We have newly realized that certain cancers have a common feature, namely that they represent an inappropriate or pathological response to activation of a hibernation pathway involved in HDS. Further, certain cancers have two features in common, namely, an infection and an inappropriate or pathological response to hibernation. In certain of these cancers, the common infection can be bacterial and in others, the infection can be viral. With this novel understanding, we have developed new methods for treating cancers.

Certain embodiments of this invention are based on the identification that several tumors have striking similarities to HDS. In turn, HDS has similarities to certain fetal conditions. Thus, in certain embodiments, treatment of tumors can be carried out using combination therapy using antibiotics to decrease bacterial infections associated with HDS, and by using other compounds to treat dormancy. Thus, the combination of antimicrobial therapy along with agents that inhibit embryonic/hibernation pathways mortalizes cancer cells allowing them to undergo apoptotic and/or necrotic cell death.

In general, aspects of this invention include determining whether a patient has a cancer and HDS. Once that determination is made, treatment with at least one antimicrobial agent and at least one anti-HDS agent is initiated. If desired, conventional therapies, including surgery, radiation treatment and/or chemotherapy can be used.

In certain of these embodiments, new regimens for using antimicrobials have unexpectedly desirable therapeutic effects, including remission or disappearance of tumors, increased life span, and other beneficial effects. In some circumstances, use of antibiotics can produce a Jarish-Herxheimer reaction, in which bacterial products, such as endotoxin, are released into the body. Such products can drive the host's immune system and metabolic system deeper into HDS, thereby protecting the invading microorganisms. By recognizing this relationship and using unique tools to eliminate these antigens, we further the process of reversing the immortalization process associated with cancer and autoimmune disease while we address the related intracellular infections.

Additional embodiments include use of agents used to treat HDS. For example, Ursodiol can be used to restore bile volume and improve clearance of microbial toxins, lipase to digest lipid A from the bile, plaquenil can be used to block TLR's and restore mitochondrial membrane permeability. Iodine- or iodide-containing compositions can be used to normalize rT3/fT3 ratio, and magnesium can be used to maintain metabolic integrity, vitamin C can be used in doses that are appropriate for the increased oxdative stress associated with Jarish Herxheimer reactions, and mineral mixtures along with hyperthermia can enhance cutaneous elimination of toxic antigens.

Effects of these measures include preservation of immune function, blood pressure, Stage 4 sleep, optimal pH, mitochondrial function and mineral balances that reverse dormancy throughout the host as well as in the targeted immortalized cells. In the traditional sense, the antibiotic is applied and if the endotoxin levels reduce blood pressure, a systemic blood pressure-enhancing therapy is initiated. This practice does not offset the metabolic slowing associated with dormancy nor does it stimulate or preserve non-dormant immune function. Traditional therapy is not focused on treating chronic illness such as cancer or autoimmune disease by restoring apoptosis or necrosis of infected cells.

In contrast, in embodiments of this invention, once an endotoxin response has been observed and has abated to a tolerable level, the dose of the antibiotic can be increased rather than decreased. This counter-intuitive step permits the antibiotic to enter cells harboring infective agents and can kill the agents within the cell, and therefore initiate cell death. Certain cancers are associated with intracellular infections. Thus, by use of the counterintuitive step of increasing the antibiotic dose at a time in which the symptoms of systemic infection are abating, one can effectively treat autoimmune disorders or cancers.

What is currently recognized as stress-influenced, noninfectious autoimmune disease is a process related to human dormancy syndrome with secondary exacerbation by lipopolysaccharide ("LPS") (or other superantigen) producing organisms, especially *Chlamydia pneumoniae* (Cpn), *Mycoplasma pneumoniae* (Mpn), *Helicobacter pylori* (Hpi), herpes virus such as Herpes Simplex Virus 1 & 2 (HSV-1 & HSV-2), Herpes Zoster (HHV-3), Epstein-Barr (EBV or HHV-4), Cytomegalovirus (CMV or HHV-5), Human Herpes virus-6 & 7 (HHV-6 & HHV-7) Human Parvovirus B19 (HPV-B19), Human Papilloma virus (HPV) and/or fungal infections. Diagnosis and treatment of autoimmune disease can benefit from testing and treatment of human dormancy syndrome, cancer, Cpn, Mpn, HHV and fungal infections.

In certain aspects, this invention includes devices useful for detection of HDS. Such devices include biochips, which may include a surface (e.g., glass or plastic) to which are attached molecules capable of binding to one or more markers of HDS ("detection molecules"), and thereby enabling detection of the marker. Such "HDS biochips" may include other molecules useful for detecting cancer. Such combination biochips can be made according to methods known in the art.

In additional aspects, this invention includes therapeutic compositions, including one or more antimicrobial agents and one or more anti-HDS agents. These compositions may be administered to a patient suffering from a HDS-related cancer.

BRIEF DESCRIPTION OF THE FIGURES

This invention is described with respect to several embodiments thereof. Other features can be found with reference to the Figures, in which.

DETAILED DESCRIPTION

Figure 1:
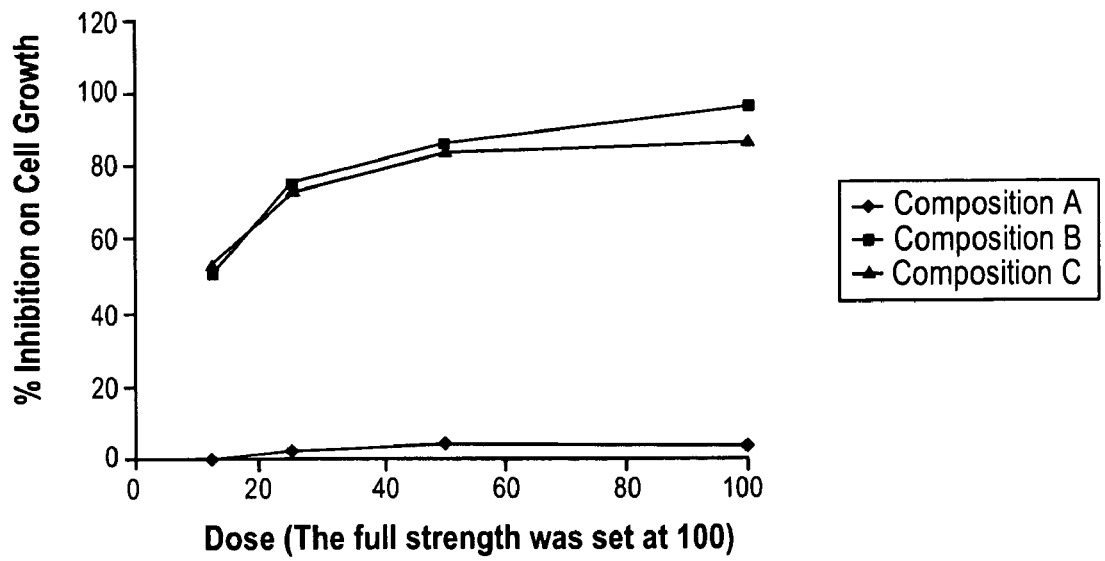
FIG. 1 depicts a graph of dose of compositions of this invention versus % inhibition of growth of 3T3 murine fibroblast cells.

Embodiments of this invention are based upon the surprising findings that certain types of cancers are associated clinically and pathophysiologically with infection by bacteria, for example, *Mycobacteria* or *Chlamydia pneumoniae*. Based on this finding, improvement in cancer therapy can be accomplished by treating the bacterial infection. In some cases in which conventional anti-cancer therapy has failed, treatment of bacterial infection can, without other intervention, result in remission of the cancer. In other embodiments, additional therapy using anti-HDS compositions can be especially useful.

Diagnosis of HDS-Related Conditions

Measurement of the rT3/fT3 ratio, nitric oxide levels, DHEA-S, free testosterone, estriol, estradiol levels or other variables denoted in Table 1 are helpful for the purposes of diagnosing HDS, and numerous clinical and biochemical tests, including diagnostic markers can be measured and can indicate presence of cancers associated with infections by Cpn, Mpn, Hpi, HHV and fungi.

In particular, as disclosed in U.S. Pat. No. 7,288,257, incorporated herein fully by reference, rT3/fT3 ratio was measured in a group of 5 normal, athletic, healthy females, selected based upon general fitness and levels of activity. Serum rT3 and fT3 were measured using standard methods. The average ratio of rT3 to fT3 was 4.18±1.08 (Standard Deviation). The standard error of the mean (SEM) was 0.48 (n=5). Finding a rT3/fT3 ratio greater than about 4 therefore correlates with HDS.

Additional aspects of HDS are described in U.S. patent application Ser. No. 11/206,564, filed Aug. 18, 2005, now U.S. Pat. No. 7,485,298, issued Feb. 3, 2009, which claims priority to U.S. patent application Ser. No. 10/444,845 (now U.S. Pat. No. 7,288,257), filed May 23, 2003, which claims priority to U.S. Provisional Patent Application Nos. 60/382,913, filed May 23, 2002 and 60/383,271, filed May 24, 2002 and U.S. patent application Ser. No. 11/975,216, filed Oct. 18, 2007, now U.S. Pat. No. 7,648,704, issued Jan. 19, 2010, which claims priority to U.S. patent application Ser. No. 10/444,845 (now U.S. Pat. No. 7,288,257), filed May 23, 2003, which claims priority to U.S. Provisional Patent Application Nos. 60/382,913, filed May 23, 2002 and 60/383,271, filed May 24, 2002. Each of the above patent applications and the patent are herein expressly incorporated fully by reference as if separately so incorporated.

Measurement of sympathetic nervous system hyperactivity using electronic devices designed to measure "stress", such as biofeedback machines, could also be beneficial for diagnostic purposes. In addition, it can be useful to measure heat-shock proteins (HSP), especially cHSP60 from *Chalamydia* using ELISA, Western blotting, Southern blotting or other methods know in the art.

In further embodiments, it can be useful to measure activity in the kynurenine pathway. For example, IDO RNA, IDO activity in leukocytes, tryptophan:kynurenine ratio, serotonin, melatonin and quinolinic acid. Measurement of these variables can also be used to monitor progress of treatment. Further, measurements of moesin levels in tissue or leukocytes and fatty acid synthase (FAS) by PCR or other methods can be useful.

It can also be desirable to test for organisms that can initiate and/or maintain HDS. Such organisms may act via the moesin, kynurenine, CD14, or Toll-Like Receptor (TLR) pathways. Such organisms include *M. avium-intracellulare, M. kansasii, M. xenopi, M. malmeonse, M. fortuitum, M. Chelonei, M. ulcerans, M. tuberculi, Bacillus Burgdoreri, B. henselae, T. whipelli, Chlamydia pneumoniae, C. psitaci, C. trachomatis*. Certain viral infections can contribuitre to HDS by production of interferon-gamma. Viruses include HHV6, HHV7, Epstein Barr virus, cytomegalovirus (CMV), human immunodeficiency virus (HIV), Herpse Zoster, Herpes Simplex virus 1 (HSV-1), HSV-2) and Simian virus.

Fungi can also contribute to HDS. These include *Aspergilus, Penicillium, Candida, Alternaria, Cladosporium* and *Mucor.*

Hibernating animals express a biochemical phenotype that is remarkably similar to the cellular changes observed in animal tissue during embryonic development, endotoxemia, cancer, autoimmune disease, and other conditions associated with oxidative stress (Table 1).

TABLE 1

Expression of Cellular Proteins in Various Conditions of HDS

| | Fetal | Hibernation | Endotoxin | Cancer | Autoimmune | FM |
|---|---|---|---|---|---|---|
| ACE II | Up | Up | Up | Up | Up | ? |
| acetyl CoA carboxylase (ACC) | Up | dec | dec? | Up | ? | ? |
| Adrenal insufficiency | N/A | Up | Up | Up | Up | Up |
| alpha-1-antitrypsin | Up | Up & down | Up, then dec | Up, then dec | Up, then dec | dec |
| Alpha2-macroglobulin | Up | Up | Up | Up | Up | Up |
| alpha-fetoprotein (AFP) | Up | ? | Up | Up | Up | ? |
| angiotensin | Up | dec ? stage? | Up | Up | Up | Blunted response |
| Anlithrobin III | dec | ? | dec | dec | dec | ? |
| Apolipoprotein A1 | dec | Up | binds to ETX | dec | dec | ? |
| Ascorbic Acid | Up beyond maternal | Up | dec | dec | dec | dec? |
| Bcl-2 | Up | Up | Up | Up | Up | ? |
| Bcl-xL | Up | Up | Up | Up | Up | ? |
| beta-endorphin | Up | dec | Acute Up | dec | Up (acute) dec (Chron) | |
| c-fos | Up | Up | Up | Up | Up | Up |
| c-jun | Up | Up | Up | Up | Up | ? |
| C1-esterase inhibitor | Up? | ? | dec | dec | dec | ? |
| calcitonin gene-related peptide (CGRP) | Up? | Up | Up | Up | Up | Up |
| calsequestrin | Up | Up | ? | Up | ? | ? |
| cAMP | Up | Up | Up | Up | Up | ? |
| Carcinoembryonic antigen (CEA) | Up | ? | Up | Up | Up? | ? |
| caspase | dec | ? | dec | dec | dec | ? |
| catalase | Up | Up | Up | Up | Up | Up |
| Cathepsin B (serine protease) | Up | Up | Up | Up | Up | ? |
| caveolin-1 | dec | ? | dec | dec | dec | ? |
| Cholecystokinin (CCK) | Up | varies | Up | Up | ? | ? |
| cIAP-2 (cellular inhibitor of apoptosis-2) | Up | ? | Up | Up | ? | ? |
| connexin 43 | Up | Up | Up | Up | Up | ? |
| corticotropin-releasing factor (CRF) | Up | Up | Up | Up | Up | Up |
| cyclooxygenase-2 (COX-2) | Up | ? | Up | Up | Up | ? |
| cystatin (C inh cathespins) | varies | ? | dec | dec | dec | ? |
| cytochrome-c oxidase | dec | dec | dec | dec | dec | dec |
| D-dimer | Up | ? | Up | Up | Up | ? |
| Dopamine (Vit C dependent) | Up | Up | dec | dec | dec | dec |
| endothelin-1 | Up | Up | Up | Up | Up | Up |
| endotoxin | ? | ? | N/A | Up | ? | ? |
| Enkephalin | Up | Up | Up | Up | Up | Up |
| epithelial growth factor | Up | ? | Up | Up | Up | ? |
| Factor V | dec | dec | dec | Dec+/− | dec | ? |
| FADD (Death Domain) | Up | ? | Up | Up | Up | ? |
| fas ligand | Up | ? | Up | Up | Up | ? |
| fas/APO 1 | Up | ? | Up | Up | Up | ? |

TABLE 1-continued

Expression of Cellular Proteins in Various Conditions of HDS

| | Fetal | Hibernation | Endotoxin | Cancer | Autoimmune | FM |
|---|---|---|---|---|---|---|
| FLIP (prevents apoptosis) | Up | ? | Up | Up | Up | ? |
| fT3 | dec | dec | dec | dec | dec | dec |
| GABA | Up | Up | Up | Up | ? | ? |
| gap junction activity | Up | Up | Up | Up | Up | ? |
| Gastrin | Up | Up (neurons) | Up | Up | ? | ? |
| Ghrelin | Up | Up | Up | Up | Up | Neither |
| glutathione peroxidase | Up | Up | Up | Up | Up | Up |
| Glyceraldehyde-3-phosphate dehydrogenase | dec | dec | dec | UP!!! | Up!! | dec |
| GSH/GSSG ratio | dec | dec | dec | dec | dec | ? |
| heart type fatty acid protein (FABP) | Up | Up | ? | Up | ? | ? |
| heme oxygenase-1 | Up | Up | Up | Up | Up | ? |
| Hormone sensitive Lipase (HSL) | Up | Up | Up | Up | ? | ? |
| HPA axis dysregulation | Up | Up | Up | Up | Up | Up |
| HSP70 (Vit C dependent) | Up | Decrease | Up | Up | Up | ? |
| Hypoxia-inducible factor-1 (HIF-1) | Up | Up | Up | Up | Up | ? |
| ICAM-1 | Up | Up | Up | Up | Up | Up |
| IGF-1 (Vitamin C related) | Up | dec 75% | dec | Up | Up | neither? |
| IGFBP inh IGF-1 (inverse of Vit C) | Up | dec | Up | Up | Up | conflict n = 3 |
| IL-6 | Up | ? | Up | Up | Up | Up |
| JNK | Up | Up | Up | Up | Up | ? |
| JunB (Vit C dependent factor) | Up | Up | Up | Dec = bad | dec? | ? |
| kallikrein/kinin | Up | ? | Up | Up | Up | ? |
| lipoxygenase (5-LOX) | Up | ? | Up | Up | Up | ? |
| MAPK | Up | Up | Up | Up | Up | ? |
| Mcl-1 | Up | ? | Up | Up | Up | ? |
| Melatonin | Up | dec | dec | dec | UP!!!! | dec |
| moesin/ezrin | Up | Up | Up | Up | Up | ? |
| Na/K-ATPase | Up | decrease | decrease | varies | decrease | ? |
| Neuropeptide Y | Up | Up | Up | Up | Up | Up |
| neurotensin | Up | Up? | Up | Up | ?article pending | ? |
| NF kappa B | Up | Up | Up | Up | Up | ? |
| Nitric Oxide (Vit C dependent) | Up | Dec (varies) | both | dec | Up | ? responds to NTG |
| Nitric Oxide Synthase (Not type II) | Up | Dec (varies) | both | Up | Up | ? |
| Norepinephrine | Up | Up then decrease | Up | Up | Up | Up |
| Orexin-A/Hypocretin-1 | ?varies | dec | dec | dec | dec | ? |
| Oxytocin (tissue vs serum) | ?dec | Up in pineal | Up in hypothal. | Up & down | Up in Medulla | dec (Blood) |
| oxytocinase | | | | | | |
| pancreatic triglyceride lipase (PTL) | ?Up | Up | Up (LPL) | Up | Up (antibodies to) | ? |
| PARP | varies | ? | Up | Up | Up | ? |
| Pyruvate Dehydrogenase Kinase (PDK) | ?Up | Up | ? | Up | ? | ? |
| peptide YY | Up | Up? | Up | Up | Up | ? |
| PPAR gamma | Up | Up | dec | Both | Both | ? |
| Prolactin | Up | Up | dec then Up | Up | Up | Up |
| prostacyclin | Up | ? | Up | Up | Up | ? |

TABLE 1-continued

Expression of Cellular Proteins in Various Conditions of HDS

| | Fetal | Hibernation | Endotoxin | Cancer | Autoimmune | FM |
|---|---|---|---|---|---|---|
| PGE2 (Vit C dependent faCtor, inverse relation) | Up | dec | Up | Up | Up | Up |
| Protein kinase C (Vit C deactivates) | Up | dec | Up, then down | Up | Both | Both |
| Resistin | Up | Up | Up | ? | ? | ? |
| Rho-kinase (ROCK-2) | Up | ? | Up | Up | Up | ? |
| rT3 | Up | Up | Up | Up | Up | Up |
| ryanodine receptor | Up | Up | dec | ? | Up from NO | ? |
| Secretin | Up | dec | dec | Some Cells Up | ? | ? |
| Serine (matrix) Protease | Up | ? | Up | Up | Up | ? |
| Serotonin (Vit C dependent) | decr | decr | Up, then decr | dec? | Up from platelets | dec |
| Substance P | Up | Up | Up | Up | Up | Up |
| superoxide dismutase | Up | Up | Up | Up | Up | Up |
| survivin | Up | ? | Up | Up | Up | ? |
| Taurine | Up | Up | Up | Up | Up | depleted |
| thrombin-antithrombin complex (TAT) | Up | ? | Up | Up | Up | ? |
| Thyrotropin-releasing factor (TRH) | ?varies | dec | dec | Up on CA cells, serum? | ? | ? |
| thyroxine binding globulin | Up | Up | ? | dec | dec | ? |
| TNF alpha | Up | Up end of hiber | Up | Up | Up | Up & Normal |
| TRAIL | ?Up | ? | Up | dec? | both . . . see decoy | ? |
| tyrosine hydroxylase | Up | Up | Up | Up | Up | ? |
| UCP2 & 3 | ? | Up | Up | Up & normal | ? | ? |
| Vasoactive Intestinal Peptide (VIP) | Up | Up | Up | Up | Up | Up |
| Vasopressin | Up | Up | Up | Up | Up | +/- |
| VEGF | Up | Up | Up | Up | Up | Up if (+) IC |

The presence of the fetal protein moesin in hibernation, cancer and autoimmune disease strongly implicates a similar metabolic process since it is rarely, if ever present in healthy fully-developed summer active animals. Additional clues exist linking embryonic pathways to cancer and autoimmune disease and these include elevated alpha-fetoprotein, and carcinoembryonic antigen levels in which are frequently elevated in fetal tissue, cancer, and autoimmune disease processes.

It is our new contention that all animals enter dormancy in utero, and this process is partially mediated by the placental production of rT3 that exceeds that in the maternal circulation. Animals that are handicapped by aberrant ascorbic acid metabolism cannot enter, maintain or exit the dormant state.

Striking similarities include the presence of moesin in all conditions. Moesin is a fetal protein that is absent in aroused hibernators but elevated during hibernation. Moesin is elevated in cancer, autoimmune disease and most importantly, it is a receptor for lipopolysaccharide (LPS) (also known as endotoxin) interacting with CD14 and Toll-Like Receptor 4 (TLR4), TLR2, TLR3, TLR9 or other of the 13 known TLRs to trigger the inflammatory cascade. Endotoxin (ETX) is a remarkably conserved bacterial and fungal surface membrane component that is released into the host during infection. Lipid A is the superantigen component of LPS and this moiety has been associated with lethal septic shock, asthma, cancer, autoimmune and heart disease. It is LPS through its interaction with the hibernation mediators moesin, CD14, and TLRs such as TLR4 that initiate HDS and its sequellae.

Viral antigens can interact with TLR's 3, 7, 9 and can initiate dormancy within the host immune system and can suspend apoptosis within the host cell they inhabit. TLR's are an embryonic necessity, and the first 5 years of TLR research focused on this relationship. When TLR's were unexpectedly found to bind endotoxin, a presumption was made that persists to date, that TLR's recognize infections and by binding to infectious antigens helps the host to respond to these infections.

The limitations of this theory are two fold: firstly it appears to conflict with evolutionary biology to suspect that bacterial endotoxin and HSP would not change dramatically and reduce TLR binding if the interaction between TLR and endotoxin served the host and lead to reduced survival of the bacterium. Many endotoxin producing microorganisms reproduce multiple times per hour and mutate readily, which explains their ability to develop drug resistance so rapidly. This means bacteria are more versatile than the cells they infect and would easily change endotoxin if it was working against them. Secondly, it is difficult to explain why mammals would use their embryonic TLR's, receptors that are involved in suspending apoptosis, to recognize infections. The recognition of HDS provides a mechanism that is the distinct from the currently held belief about infection and TLR's, and this new recognition creates the potential for more effective treatments than those that are currently available.

The logic of the new understanding is straight forward: humans are mammals and all mammals have the hibernation receptors and pathways, whether or not they use them to hibernate. This is supported by the finding that most mammalian embryos require a placenta and must survive for a period of time without one, prior to formation of a functional placenta (about 4 weeks). To survive in an environment without adequate glucose or oxygen for days to weeks requires suspention of apoptosis, and this is mediated through the TLR's. Increased levels of Bcl-2, an immortalization gene and peptide, have been observed in preimplantation porcine embryos. It would not be possible to survive embryonic life without TLR's and the capacity to suspend apoptosis. This mechanism is used during hibernation to allow the mammal to survive in an environment without adequate food or warmth. Immune function is weaker in hibernation than it is in the summer active months, with reduced cellular immunity and what appears to be a compensatory increase in the production of inflammatory molecules. During hibernation the increase in NF kappa B levels can lead to increases in the inflammatory superfamily of genes that manufacture TNF-alpha. Compromised immune function with reductions in cellular immunity favors bacteria, viruses and fungi, all of which can synthesize antigens that stimulate TLR's and initiate hibernation in the mammal's immune system.

The reduction in T-cell activity would be incentive enough for microorganisms to target our TLR's, but there can be another incentive. Children undergoing heart surgery have been found to have dramatically elevated serum endotoxin levels approximately 1,800% greater than baseline levels. In a recent study of 93 children undergoing cardiac surgery, urine iodine levels were found to increase by 7,000%. The massive ioduria would not serve the host because iodine is immune enhancing and deadly to bacteria, virus and fungi. Iodine is metabolically stimulating and it is likely that iodine could impede the metabolic slowing necessary for hibernation. The massive excretion of iodine during hibernation is predictable, and since endotoxin can be a false signal to hibernate, it is now not surprising that this occurs during endotoxemia in humans. Iodine is still a bacteriocidal agent of choice in the surgical setting and the dramatic elimination of iodine from mammalian tissues would not serve the host. Massive ioduria serves the infection by further impairing the innate immunity of the host.

Until now, medical science has over-looked the central importance of our hibernation pathways, but microorganisms have not. The most up to date medical literature is misinterpreting TLR function and proposing that TLR's are designed to recognize infections and we believe the opposite is true. The immune response observed after TLR stimulation is the hibernation immune response with dramatic reductions in cellular immunity and depleted tissue iodine levels, a response that is far less protective than what is observed in the summer active immune system. The recognition of HDS provides for novel treatments that seek to reverse dormancy and restore non-dormant immune function, which produces favorable outcomes that are not typical of today's standard of care.

The biochemical similarities between the fetal state, hibernation, cancer, autoimmune disease and fibromyalgia depicted in Table 1 are readily evident, and each of these conditions is considered part of HDS. The rare discrepancies between fetal/hibernation metabolism and human disease are directly associated with the loss of an enzyme in humans called gulonolactone oxidase (GLO). GLO is present in the genome for all animals except guinea pigs, fruit bats, and primates including man. It has been hypothesized that a retrovirus may have caused a mutation 35 million years ago impairing GLO synthesis. The result of GLO deficiency is that the final step in ascorbic acid metabolism is absent, endogenous ascorbic acid synthesis is interrupted and ascorbic acid must be obtained from a dietary source. What appear to be anomalous findings in Table 1 are predictable responses in factors that directly or indirectly require ascorbic acid for their synthesis or degradation.

During periods of health the consequences of the GLO deletion may not be as apparent as it is during periods of increased oxidative stress, a condition that increases the demand for ascorbic acid. For example, apolipoprotein A1, a cardioprotective molecule is low in atherosclerosis, endotoxemia, cancer, and autoimmune disease, but it is elevated in hibernating animals and in placental tissue. Not coincidentally, serum ascorbic acid levels are elevated in hibernating animals, especially when arousing from hibernation, and apolipoprotein A1 levels parallel ascorbic acid levels. Similarly, junB is an ascorbic acid dependent factor that is elevated in hibernating animals and animals in utero but is decreased in cancer and autoimmune diseases. Natural hibernation is associated with suppression of PGE2, HSP70, and nitric oxide levels, all ascorbic acid dependent factors, and the opposite is evident in HDS related conditions of endotoxemia, cancer, and autoimmune disease.

The presence of the fetal protein moesin in hibernation, cancer and autoimmune disease strongly implicates a similar metabolic process, since moesin is rarely, if ever, present in healthy, fully-aroused, summer-active mammals. Additional clues exist that link embryonic pathways with cancer and autoimmune disease and these include elevated alpha-fetoprotein, and carcinoembryonic antigen levels in fetal tissue, cancer, and autoimmune disease. It is our contention that all animals enter hibernation, or dormancy, in utero. Animals that are handicapped by aberrant ascorbic acid metabolism can not enter, maintain or exit dormancy properly. This is especially true of humans when dormancy is imposed on them by infection with LPS producing organisms. In such instances, the elimination of the LPS signal along with the infectious source is required to impact the sequellae of HDS. Use of the natural signals involved in the arousal from hibernation and dormancy is essential to reversal of HDS and to treat HDS-related conditions. For example, ascorbic acid levels are elevated in hibernation and especially during the arousal phase. Treatment of HDS proceeds more rapidly when ascorbic acid levels are normalized or elevated. Similarly treatment will frequently benefit from the use of agents that increase fT3 as seen in the arousal stage of hibernation and lower rT3 levels. Measurement of the rT3/fT3 ratio easily defines those who will benefit most from normalization of thyroid conversion.

Human Dormancy Syndrome Diagnosis of human dormancy syndrome can be accomplished using clinical findings (history and physical findings) and laboratory chemical tests of urine, blood, cerebrospinal fluid (CSF) and/or tissues.

Clinical Findings

Pertinent historical features include symptoms of persistent fatigue, cognitive impairment, weight gain, depression, alopecia, constipation, insomnia, sleep apnea, loss of libido, cold intolerance, exercise intolerance, addiction to stimulants, history of Raynaud's syndrome, dislipidemia, atherosclerosis, syndrome X, peripheral vascular disease, type II diabetes, Alzheimer's disease (and other dementias), demyelinating disease, (muscle tension headache, migraine), fibrocystic breast disease, breast cancer, prostate cancer, ovarian cancer, other cancers, cholelithiasis, pulmonary artery hypertension, pulmonary fibrosis, COPD, asthma, systemic hypertension, infertility, fibromyalgia, chronic fatigue syndrome, chronic wide spread pain and other chronic pain states, and obesity. autoimmune conditions such as lupus, scleroderma, rheumatoid arthritis, sarcoidosis, vasculitis, myositis, ankylosising spondylitis, psoriatic arthritis, reactive arthritis, Reiter's syndrome, Becet's and polymyalgia rheumatica, viral, bacterial and fungal infections, septic shock, pneumonia and other serous infections, narcolepsy, hypertension, liver disease, esophageal dysmotility, inflammatory bowel disease, renal disease, Parkinson's disease, coma, impaired stage 4 sleep, irritable bowel syndrome, elevated CRH, elevated sympathetic nervous system activity, dysregulated HPA, low serotonin, altered nitric oxide metabolism and NOS activity, low oxytocin levels, mitochondrial impairment and structural changes with decreased membrane permeability, compulsivity, hypervigilance, dissociation, impaired natural killer cell activity, elevated CSF substance P levels, blunted growth hormone response during provocation testing, orthostatic hypotension, altered cerebral blood flow.

Laboratory Findings

Laboratory findings can include elevated serum rT3 and/or low serum fT3 levels, elevated 5 deiodinase type II (5'-D2) activity, decreased 5'-deiodinase type II (5'-D2) activity, increased mRNA for 5'-D2, decreased mRNA for 5'-D2, increased 3,5,3' triiodothyroacetic acid, low CSF serotonin levels, low CSF melatonin levels and elevated CSF SP levels. Low serum and CSF oxytocin levels and altered citruline levels may indicate altered nitric oxide production. Low serum or salivary iodine or low iodine excretion after iodine loading is consistent with dormancy, as is hyponatremia or hypomagnesemia.

Thus, according to this invention, a proper normal range can be obtained from non-stressed individuals. By comparing the rT3/fT3 ratio of patients with HDS with a true normal range, an elevated rT3/fT3 ratio can indicate the presence of HDS. Table 2 shows effects of HDS on physiological systems.

TABLE 2

Effects of HDS on Physiological Systems

| Physiological Variable | HDS | Fibromyalgia |
|---|---|---|
| rT3 | High | High |
| fT3 | Low | Low |
| Serotonin | Low | Low |
| Melatonin | Low | Low |
| Oxytocin | Low | Low |
| Prolactin | High | High |
| Substance P | High | High |

TABLE 2-continued

Effects of HDS on Physiological Systems

| Physiological Variable | HDS | Fibromyalgia |
|---|---|---|
| HPA Axis Activity | High | High |
| Muscle Weakness | Yes | Yes |
| Exercise Intolerance | Yes | Yes |
| Memory Impairment | Yes | Yes |
| Low Oxygen Consumption | Yes | Yes |
| Female:Male Predominance | Yes | Yes |

Endotoxin Testing

The FDA has recently approved an Endotoxin Activity Assay (EAA) developed by Spectral Diagnostics, Inc. for human endotoxin testing. Spectral defines the EAA's intended use in the following manner: "The EAA test is intended to be used in conjunction with other clinical information such as clinical signs, other laboratory and/or radiographic test results to aid in the risk assessment of patients on their first day of admission to the ICU for progression to severe sepsis. Patients tested on their first day of admission to the ICU where the EAA value is >0.60, are three times more likely to develop severe sepsis within the next 24 hours than subjects whose EAA values are <0.40." The control population selected for standardization of the assay is reported as the following: "We recruited 97 healthy ambulatory volunteers from the sponsor's manufacturing facility to establish normal levels for the endotoxin activity (EA) assay." The Gaussian curve for the 97 volunteers ranged from 0.1 to 0.6 "EA level", while the graph for the ICU patients they assayed from multiple test centers had values that ranged from 0.0 to 1.0 with the vast majority of patients showing levels in the 0.2 to 0.8 range. There is significant overlap with the healthy ambulatory population. For the purposes of working with ICU patients, comparison to ambulatory patient endotoxin levels may be sufficient.

However, for the purposes of using an endotoxin assay to facilitate the diagnosis of HDS and monitor therapy for LPS related infections, the control group must exclude volunteers who are infected with HDS promoting organisms. Exclusion criteria for control subjects should include a history of HDS related symptoms (i.e.—asthma, chronic sinusitis, hypertension, arthritis, fibromyalgia, cancer). Those with low probability for HDS related infections should then be tested for Cpn, Mpn, *H. pylori*, EBV and other herpes viruses using humeral assays and DNA testing as described by Charles Stratton, MD to insure that each control subject is suitable negative control. Other tests could include measurement of eosinophil cationic protein levels, NF kappa B levels, ACE and angiotensin levels to insure that Th 1 activation is not present in the negative control group. IgG testing for fungal antigens might identify those with allergic fungal syndromes that could contribute elevated endotoxin levels. Tighter control of the reference group will allow for broader application of the EAA for the purpose of identifying those at risk for HDS and it's sequellae. Defining healthy as uninflamed and uninfected or minimally infected with LPS producing organisms is a better reference point for comparison when testing those who might have HDS related conditions.

Environmental Testing

Lipopolysaccharide (LPS) is a signal used by microorganisms to impair host immunity by engaging receptors that are normally used by the host for embryonic development and hibernation. Recognition of the nature of the LPS signal should change the way we interpret our environment. For example, endotoxin is present in most food, water and air samples. Acceptable levels of endotoxin have been established for human consumption, but these guidelines were established before there was an understanding of the potential for endotoxin to contribute to HDS and related sequellae. For example, dried tobacco leaves contain large amounts of endotoxin from fungal sources. Inhaled endotoxin directly influences pulmonary cells to shift towards fetal/hibernation metabolism with what we currently refer to as "inflammatory changes," but now recognize as the anti-apoptotic molecular changes needed for the low oxygen environments of early gestation and hibernation. Chronic exposure to the LPS signal can lead to the proliferative changes observed in early gestation, findings observed in granulomatous disease and cancer. It appears that the host may become more vulnerable to LPS producing organisms after chronic environmental exposure to LPS. In the example of tobacco use, it is likely that the endotoxin on the tobacco leaves is more oncogenic than the tobacco. Environmental LPS influences the cells it stimulates and facilitates the growth of LPS producing organisms. It is likely that the facilitated growth of LPS producing organisms in smokers leads to the chronic pulmonary disease and increased cancer incidence in smokers.

Diagnostic HDS Devices

This invention includes devices suitable for biochemical identification of HDS. In certain embodiments, a "HDS biochip" includes a surface or "detection surface" (e.g., such as glass or plastic) onto which "detection molecules" are affixed. A detection molecule may be a HDS-marker-specific antibody (IgG, IgM, IgE, Fab Fab' fragments thereof), or other antibody-based detection molecule known in the art. In other embodiments, a detection molecule may be an ologonucleotide able to bind to an RNA or DNA marker for the HDS gene product. Such oligonucleotide probes are known in the art, and novel combinations of such probes can be affixed to a detection surface. HDS markers may be selected from any of the biochemical indicators disclosed herein. For example, a HDS biochip may have detection molecules selected from Table 1m Table 2. Additionally, viral antigens can be useful to detect viral infection associated with HDS. It can be appreciated that any HDS marker may be detected using such devices, if a detection molecule for the marker is identified.

A sample of material from a patient is placed on the HDS biochip and allowed to incubate for a period of time to permit binding of the HDS markers with their detection molecules. Non-bound material is then removed by washing, and then the bound HDS markers are detected using "detection molecules," which include, in the case of antibody detection molecules, a labeled anti-Ig obtained from a different species. In the case of oligonucleotide probes, hybridization of an oligonucleotide probe for an HDS marker may be detected by Raman spectroscopy, radio labels, fluorescent labels and/or other methods known in the art.

It can also be appreciated that such devices can also be useful for detecting the HDS-associated cancer. Numerous biochemical and genetic markers are known for cancers, and combination chips that include markers of HDS and of cancer can be particularly useful.

Such devices can be used in an initial stage of diagnosis of HDS-related cancer, to determine progress of therapy, and/or as follow up diagnostic procedures to determine whether a successful treatment of a HDS-related cancer is being maintained, or whether a recurrence of the tumor has occurred.

It can be appreciated that devices of this invention can also be incorporated into kits. Such kits may contain a device as described above, solutions or incubating patient samples, solutions for washing, reagents for labeling bound HDS and/ or cancer markers, and associated supplies, including vials, stirring rods, and instructions for use.

Additional Diagnostic Features of HDS

Additional teste for HDS include measurement of the species specific HSP (i.e.—cHSP60 from *Chlamydia*) using ELISA, Western Blot, Southern Blot or other means.

Further, measurement of kynurenine pathway activity to define HDS activity using PCR of IDO RNA, measuring IDO activity in leukocytes or other tissues, measuring tryptophan: kynurenine ratio, measuring serotonin, melatonin or quinolinic acid levels. Measurement of TLR activation or gamma interferon levels may also be helpful in diagnosing dormancy because activation of these mediators increase IDO activity, thus increasing toxic kynurenine & quinolinic acid levels. These levels can be used to monitor effective treatment of HDS. Measuring moesin levels in tissue or in leukocytes can establish the activation of HDS. Measuring fatty acid synthase activity by PCR of FAS mRNA to estimate the activity of HDS. Measurement of serum hibernation Induction Trigger (HIT) levels can help to assess HDS. Examples of agents that can trigger hibernation include aspartame and flavor enhancers that signal via opioid receptors.

Intracellular signaling from LPS producing organisms such as C.pn may have a more potent anti-apoptotic effect than extracellular LPS producing organisms. Other examples include conditions associated with organic dust inhalation. Grain dust causes a condition that Harrison's Textbook of Internal Medicine describes as "virtually identical to the characteristic findings in cigarette smokers" which is seen in grain elevator employees and workers in flour or feed mills. The grain dust contains endotoxin from mold. Farmer's Lung occurs from exposure to moldy hay, which contains LPS on airborne spores. A strain of rice was recently genetically engineered in china to produce endotoxin as a rice-synthesized pesticide. It is very effective, killing the larvae of worms as they attack the crop. Since it requires 30 minute exposure to nearly 500° F. to render endotoxin inert, it is likely that ingestion of endotoxin containing rice will significantly increase in the coming years. Ingested endotoxin that is not degraded by digestive enzymes or neutralized with bile can be absorbed and enter the blood stream. LPS is a potent signal that is ubiquitous in nature and difficult to neutralize. The volume of ingested and inhaled endotoxin has increased with the industrial revolution and it is tempting to attribute the increased incidence of diseases associated with LPS and HDS with increases in endotoxin exposure. New standards for endotoxin levels in the food and beverage industry, as well as air quality monitoring for endotoxin will be necessary to properly address HDS related sequellae.

Minimizing exposure of humans to this signal by dephosphorylating LPS in water and food prior to dispensing food and beverage products to the public is one possible solution. Modification of endotoxin with binding agents prior to ingestion might also be effective. Better testing and reporting of endotoxin levels in our food supply and careful study of animals and possibly humans who ingest various levels of endotoxin should be investigated as a possible source for the increasing incidence of HDS related diseases.

Reverse T3/Forward T3 Ratio in Cancer

One surprising finding of this invention is the discovery that patients with cancer have elevated rT3/fT3 ratios. In a group of 14 patients with various cancers, rT3/fT3 ratios were determined. The results are shown below in Table 3 below.

TABLE 3

RT3:FT3 Ratios in Cancer Patients

| Patient Age/Gender | CA Diagnosis | Stage | rT3/fT3 |
|---|---|---|---|
| 63 yrs; male | Metastatic Papillary Thyroid | — | 23 |
| 57 yrs; male | Prostate | — | 7.25 |
| 53 yrs; female | Pancreatic | — | 14.6 |
| 44 yrs; male | Metastatic Colon | IV | 9.14 |
| 65 yrs; male | Metastatic Prostate | — | 14.6 |
| 42 yrs; female | Metastatic Colon | — | 27 |
| 45 yrs; female | Lung Adenocarcinoma | — | 6.54 |
| 56 yrs; female | Metastatic Cholangiocarconoma | — | 13 |
| 56 yrs; female | Breast | — | 13.7 |
| 44 yrs; female | Metastatic Breast | — | 10.5 |
| 60 yrs; female | Infiltrating Ductal Carconoma | — | 8.4 |
| 48 yrs; female | Ovarian | IIb | 7.8 |
| 63 yrs; female | Non-Small Cell Carcinoma | III | 16 |
| 58 yrs; female | Pancreatic | I | 8.1 |
|  | Average |  | 12.8 |

These results indicated that of the 14 patients in the group, all had rT3:fT3 ratio of greater than 4, and in 11 of the 14, the ratio was more than twice the normal. In 7 of 14, the ratio was more than three times the normal value of about 4. Thus, the finding of elevated rT3:fT3 ratio is a consistent finding in patients with a variety of cancers and of cancers in different stages.

Thus, one therapeutic goal in these patients is to normalize the rT3/fT3 ratio. This can be done using a iodine- or iodide-containing composition, such as Iodoral. However, in patients with thyroxine-sensitive tumors, it can be undesirable to use T3 itself, because that could increase growth of the tumor. However, normalization of rT3/fT3 ratio can be produced by increasing production of fT3 by stimulating enzymes responsible for its formation. Because those enzymes are iodine-dependent, use of iodine- or iodide-containing compositions can be therapeutically valuable.

Treatment of HDS

In certain aspects of this invention, a therapeutic goal is to block one or more HDS related signals and signal arousal from dormancy. A general goal is to block HDS-inducing signals until HDS-inducing organisms can be cleared. For these purposes, one can use one or more of luteolin, apigenin, betulinic acid, etomoxir, GMDP, Crysin, EGCG, L-theonine, Brassinin, 1-Methyltryptophan, Provigil, Requip, Mirapex, Rozerem, melatonin, serotonin, SSRI's, SSRB's, 5-HTP, GABA, amphetamine, low dose naltrexone, T3, iodine- and/or iodide-containind compounds, omega 3, 6 or 9 oils, DHA, borage oil, vitamin E, Vitamin K, Vitamin D, Vitamin A, Vitamin C, Vitamin B12, CoQ10, alpha-lipoic acid, NADPH, Niacinamide, or other B vitamins, carnitine, pyruvate or creatine, I3C, Chorella, zinc, chromium, molybdenum, ribose, iodine and/or iodide, low dose naltrexone (LDN) or heparin. These agents can be administered orally or via injection. Thus, these agents can be useful to influence metabolism for the purpose of treating HDS-related sequellae including cancer, autoimmune disease, neurologic disease, autism or any other process mediated through moesin, CD14 or TLR pathways since these are clearly HDS-related.

Hormones can also be used to promote arousal in individuals who are undergoing treatment for HDS-related conditions. These include using one or more of oxytocin, testosterone, estrogen, estrone, estradiol, estriol, progesterone, pregnenolone, growth hormone, and somatostatin.

Agents that improve insulin sensitivity can also be desirably used, because since insulin sensitivity is contrary to hibernation and impairs a cell's ability to persist in hibernation. Such agents include one or more of metformin and glipizide. Agents that block fatty acid synthase (FAS) may also be useful because hibernating cells require FAS to maintain hibernation and blocking of FAS forces arousal/differentiation or apoptosis of hibernating/embryonic cells. Etomoxir is one potent inhibitor of FAS, as well as luteolin and EGCG also have FAS inhibiting properties and therefore can be useful for the purpose of ending HDS and treating HDS-related sequellae. Olestra is also a potent FAS inhibitor and can be delivered either orally or via patch. Patches may be desirable in that higher concentrations can be delivered through a lipophilic transdermal patch without the gastrointestinal side-effects of oral administration.

Other agents that reverse and therefore treat HDS pathways include trimetazidine, ivabradine, ranidazine, fasudil and nicorandil.

Agents that inhibit or block the kynureinine pathway can be used for inhibiting dormancy and treating HDS-realted sequellae. Such agents include but are not limited to niacin, niacinamide, inositol hexanicotinate, brassinin, heparin, 1-MT which specifically target IDO (indolamine 2,3 deoxygenase). These can be used individually or in combinations of two or more.

Agents that inhibit or block opioid receptors can be used to inhibit or block the binding and signaling of HDS that occurs when HIT binds with opioid receptors. Thus far, one agent for this purpose is LDN, although it is currently being used for purposes other than blocking HIT or reversing HDS.

Antimicrobial therapy can be accomplished using one or more of amoxicillin, azithromycin, biaxin, doxycycline, minocin, rifampin, rifabutin, metronidazole, tinidazol, ethambutol, telithromycin in combination can be used to treat HDS. Additionally, agents that influence viral infections that engage the dormancy related pathways (often via the kynurenine pathway) include but are not limited to valtrex, valganciclovir, acyclovir, ampligen, isosine, heparin, Lovenox and fondaparinux.

Components of mother's milk, especially colostrums can be used. Mother's milk contains a variety of therapeutic molecules. These molecules have not been recognized until now as a means for ending dormancy and the only available literature related to these substances broadly categorize them as immune enhancing substances. These include but are not limited to transfer factor, 2-fucosyllactose, lacto-N-fucopentaose I, lactoferrin, motilin, superoxide dismutase, amylase, alkaline phosphatase, EGF and IGF-1, Osteoprotegerin, TGF-beta, oxidative burst promoting factor(s), oligosaccharides, secretory carbonic anhydrase isoenzyme VI, opioid peptides, antihypertensive peptides, casein phosphopeptides, alpha- and beta-lactorphins and albutensin, nerve growth factor, transforming growth factor, angiogenin, fibroblast growth factor. These agents can be used singly or in combinations of two or more.

Certain plant-derived substances can also be used to treat HDS. These include one or more molecules isolated from broccoli, cabbage, green leafy vegetables, wheat grass, alfalfa sprouts, brussell sprouts, asparagus, artichoke, tea leaves, oregano leaf and oil, garlic, olive leaf or late winter crops that contain high concentrations of molecules that reverse hibernation pathways.

Treatments for viral infections can also be used to treat HDS sequellae. Immunovir, ampligen, valtrex, acyclovir, famvir, valgancyclovir, gancyclovir, vistide, heparin and related compounds are examples of agents that can reverse HDS and treating HDS-related sequellae since these agents treat infections that can propagate HDS.

As noted elsewhere herein, agents that abrogate the effects of endotoxin, HSP, viral or fungal antigens and other hibernation-inducing signals on the liver and other tissues can be used. The liver is of central importance in natural hibernation, and it is easily influenced while filtering the endotoxin released from bacterial sources. Specific agents which decrease accumulative effects of hibernation on the liver include ursodeoxycholic acid, tauroursodeoxycholic acid, choline, phosphotydalcholine and other agents that reduce the viscosity or increase the volume of bile production.

Moreover, combination therapy using anti-hibernation substances luteolin, curcumin, niacinamide, ascorbic acid or analogs of these compounds alone or in combination with antibiotics such as rifampin, ethambutol, isoniazide, minocin, doxycycline, azithromycin, amoxicillin, metronidazole, tinidazole, and acyclovir for the treatment of HDS related disease.

Treatment of HDS-Related Cancers

Certain therapeutic embodiments of this invention are directed to (1) restoring normal levels of the variables listed in Table 1, along with antibacterial and/or antiviral agents in sufficiently high doses to kill intracellular bacteria and other pathological organisms.

Embodiments of this invention are based on the surprising finding that in many types of cancer, opportunistic infections with *Chlamydia* (including *Chlamydia pneumoniae* ("Cpn")) are present. Embodiments of this invention are also based upon the surprising finding that many types of cancer are also associated with Cpn are also associated with elevated rT3/fT3 ratio, and thus are related to HDS.

Additional embodiments of this invention are based on the unexpected finding that Chlamydial infections are often associated with HDS. These observations have led to the surprising results that many types of cancer can be effectively treated using anti-Chlamydial agents along with other, conventional antitumor therapies. In other embodiments, co-therapy using anti-Chlamydial agents and treatment for HDS can decrease progression of cancer, can decrease symptoms and in some cases, can eradicate all trace of cancer from subjects suffering from many types of cancers.

Thus, in certain embodiments, cancer therapy can be improved by treatment with antibiotics. In particular, in certain embodiments, metronidazole can be used. In prior methods to treat bacterial-associated disorders, the dose of antibiotic has been limited to avoid the undesirable effects of rapid bacterial killing (Jarisch Herxsheimer or "JH" reaction). However, we unexpectedly found that by selecting patients in whom the adverse reaction has been managed through decreasing endotoxin levels, further increases in doses of antimicrobials, including antivirals, can be administered that can induce killing of tumor cells. These results have been shown in a series of patients with differing types of tumors.

LPS has been found to stimulate cancer cell growth and impair immune function therefore concomitant treatment with endotoxin (LPS) binding agents, plasmophoresis, dephosphorylating agents or other LPS neutralizing agents are an expected adjunct to the treatment of LPS induced HDS. Other measures include but are not limited to the use of agents that reduce the activity of TLR's, Bcl-2, Bcl-xL, gamma-interferon, HIT, NF kappa B, kinin, angiotensin (i.e.—ACE inhibitors or ARB's), reduce the activity of COX-2 and PGE2 (i.e.—NSAIDs or omega 3 oils), increase junB activity or lowers HSP70 activity (i.e. ascorbic acid), or increase oxytocin or nitric oxide levels (i.e.—oxytocin, nitroglycerine, Viagra). Treatment with LPS neutralizing agents should be implemented prior to the in vitro studies of the fibroblast cell line 3T3 cells and the Capan-1 human pancreatic onset of cancer, bacterial or fungal cell apoptosis inducing therapies.

In cancer cell lines, I found that a combination of antimicrobials and anti-dormancy agents can substantially kill the cells in culture in a synergistic fashion. This totally unexpected finding provides new strategies for treatment of even difficult-to-treat cancers.

Therapy also can be directed toward normalizing rT3/fT3 ratio, as noted above. Use of iodine- and/or iodide-containing compositions can be valuable to achieve this therapeutic goal.

Therapy is directed at reversal of fetal metabolism and hibernation would include more than one of the following: lowering ACE activity, increasing alpha-1 antitrypsin levels, lowering alpha 2-macroglobulin levels, lowering alpha-fetoprotein levels, lowering angiotensin II levels, increasing antithrombin III levels, increasing apolipoprotein levels, increasing ascorbic acid levels, lowering Bcl-2 levels, lowering Bcl-XL levels, increasing Bax, Bid and Bad levels, lowering c-fos and c-jun levels, increasing C1-esterace inhibitor levels, lowering CGRP and calsequestrin levels, lowering CEA levels, increasing caspase, lowering catalase and cathespin B levels, increasing caveolin-1, lowering cIAP-2 levels, decreasing connexin 43, decreasing CRF and COX-2 activity, increasing cystatin, increasing cytochrome-c oxidase, decreasing d-dimer, increasing dopamine levels, lowering endothelin-1, and especially lowering endotoxin levels; lowering enkephalin and epithelial growth factor levels, increasing Factor V levels and decreasing FADD, lowering fas ligand and the fas/APO 1 ratio, lowering FLIP, increasing fT3, lowering gap junction activity, lowering gastrin levels, lowering ghrelin levels and glutathione peroxidase levels, increasing glyceraldehyde-3-phosphate dehydrogenase activity, increasing the GSH/GSSG ratio, decreasing the FABP, lowering heme oxygenase-1 levels, lowering hormone sensitive lipase levels, lowering HSP70, lowering HIF-1 levels, lowering HIT (hibernation inuction trigger) levels or blocking the opioid recepectors that HIT normally stimulates, lowering ICAM-1 levels, lowering IGF-1 and increases IGFBP, lowers IL-6 and JNK levels, and increases junB levels, lowers kallikrein and kinin levels, lowers lipoxygenase levels, lowers, MAPK and Mcl-1 levels, increases melatonin levels, and most importantly interruption of the activation of the meosin-ezrin system; increasing the Na/K—ATPase activity, lowing neuropeptide Y and neurotensin levels, lowering NF kappa B levels and increasing nitric oxide levels, increasing orexin-A and hypocretin-1 levels, increasing or lowering oxytocin levels, increasing p53 levels, lowering pancreatic triglyceride lipase levels, increasing PARP levels, lowering PDK levels, lowering peptide YY levels, increasing PPAR gamma levels, lowering prolactin levels, lowering prostcyclin levels, lowering PGE2 levels, lowering protein kinase C and resistin levels, lowering rT3, and increasing ROCK-2 levels, increasing secretin, lowering serine protease levels, increasing serotonin levels, lowering substance P levels, lowering superoxide dismutase and survivin levels, lowering TNF alpha levels, increasing TRAIL activity, lowering tyrosine hydroxylase activity, lowering UCP2 & 3 activity, lowering VIP and vasopressin and VEGF levels.

These mediators of embryonic and dormancy metabolism can be lowered with competitive antagonists, binding proteins, proteasome inhibitors, dephosphorylating enzymes, and other fractionating enzymes or inhibitors such as MG132 which inhibits NF kappa B activation.

Endotoxemia is characteristic of infections associated with cancer. Thus, one therapeutic objective is to reduce the levels of endotoxin in the blood. However, one problem with treating endotoxemia is that the liver may be damaged and bile production may decrease. Thus, in some embodiments, new thereapeutic approaches to maintaining bile production can be desired.

Maintaining Bile Production

In certain aspects of this invention, it can be desirable to promote hepatic removal of microbial products from the body. For example, treatment of bacterial infections can produce a JH reaction, that in some cases, can be severe or even life-threatening. Thus, one therapeutic goal of the methods of this invention is to promote production of bile by the liver, and promote its secretion into the alimentary canal for removal from the body. Additional aspects include use of agents that sequester bile components to inhibit or prevent their resorption by the body.

The use of agents to reverse hibernation/dormancy (HDS) is not currently a component of allopathic or natural medicine practices. In nature, the liver is usually the last organ to freeze and is likely the orchestrator of most of the systemic adaptations to hibernation. It increases glucose and insulin levels in the hibernating animal, presumably to have a ready supply of energy available for cells during the thaw. With this in mind, an important distinction can be made between natural hibernation and infection induced dormancy/HDS; the liver is likely the first organ to be influenced in the later. This point has treatment associated implications. The liver filters endotoxin/HSP60/mycotoxin and other CD14-TLR4 associated bacterial antigens/signals as well as viral and fungal antigens that can stimulate the intracellular TLR's all of which can signal the liver to initiate dormancy.

In dormancy, the liver can:

1.) prepare the individual for dormancy by reducing metabolic rate (at least by increasing rT3 levels);

2.) reduce bile production, but it can not increase ursodeoxycholic acid levels as bears do during dormancy and the reduced bile pool becomes more viscous and the liver's filtering capacity is reduced. This can lead to higher levels of endotoxin in the biliary system, Kupfer cells and hepatocytes, which results in increased dormancy signaling for the liver. This positive feed back loop is pathological.

3.) serve as an orchestrator of dormancy and the is filter of infectious toxins; this is an important consideration for therapy. When the liver shifts towards dormancy due to increasing influences of exogenous dormancy signals (endotoxin and HSP60), the rest of the body can follow.

For these reasons, it can be desirable to prevent the liver from falling under the influence of endotoxin and other infectious antigens, from entering dormancy despite its need to filter endotoxin during therapy. An essential component of liver function to preserve is something that is not assayed for or currently considered relevant in traditional medicine—the volume and viscosity of the bile pool. Any substance that causes lowering of bile production (endotoxin, HSP, mycotoxin, saturated fatty acids, sucrose, excitatory toxins that increase glutamate release such as MSG, aspartame and other flavor enhancers, HIT) will contribute to the deepening of HDS and negatively influence HDS related sequellae. The opposite appears to be true; by maximizing bile volume and lowering viscosity the concentration of dormancy signals is lowered and the deepening of HDS is prevented. Measures that help to this ameliorate this problem includes treatment for HDS-related sequellae using one or more of the following:

1.) Ursodiol, tauroursodeoxycholic acid, choline and/or lecithin supplementation, 2.) Unsaturated oil supplementation (e.g., olive oil, omega 3 oils and/or flax seed), 3.) Milk thistle and or silymarin supplementation, 4.) Dietary modification to avoid saturated fats, especially hydrogenated oils, 5.) Ascorbic acid supplementation (necessary for the synthesis of ursodeoxycholic acid), 6.) Phlorizin, glucagon, metformin or taurine supplementation to increase bile production, and/or 7.) Herbs which increase bile production including: violets, chickweed, dandelion, sorrel, chicory, malva, mustard greens, nettles, watercress, Artemesia capillaries, gardenia, rhubarb, scute, Echinacea root, epimendium leaves, burdock root, eucommia bark, ginger, artichoke, and the flavonol luteolin.

Useful doses of the above agents can lessen the reduction of bile volume and the increase of viscosity during HDS may vary depending on the stage of treatment and the load of bioactive antigens being released as organisms are killed with antimicrobial therapy.

Ursodeoxychyolic acid (ursodiol) is a powerful hibernation blocker. Ursodiol thins the bile and awakens the liver from hibernation, and can reverse hibernation by lowering the concentration of endotoxin within the liver and biliary systems. Ursodiol also can have anti-inflammatory properties. It also can lower cholesterol levels and can improve other disorders, including Alzheimer's disease and Huntington's disease.

Other agents useful in treating HDS-related cancers include provigil, rozerem, trimetazisine, ivabradine, ranidazine and fasudil.

Agonists that increase the activity or concentration of these biochemicals may include biologically engineered analogs or agents that block inhibitory pathways. Many examples of such agents are well known in the art and need not be described in detail herein.

In general, therapy is designed to first kill systemic, extracellular infections organisms. When this occurs, bacterial endotoxins are released into the body and are associated with several symptoms. Symptoms of sepsis or endotoxemia include hypotension, headache, insomnia, malaise, tachycardia, fever, chills and then hypothermia, lymphadenopathy, palor, cognitive impairment, seizure, nausea, diarrhea and emesis among others. However, the scope of this invention is not limited to determining the presence of only the above symptoms. Other symptoms and measured variables are known in the art and are included as part of this invention.

Adjunct treatment that facilitates recovery form HDS may also include agent that lower angiotensin, kinin, ACE levels, Bcl-2, Bcl-xL, CGRP, cIAP-2, cathespin B, connexin 43, COX-2, endothelin-1, epithelial growth factor, FLIP, glutathione peroxidase, HSL, HSP70, HPA-related sympathetic activity, ICAM-1, Interluekin-1, 6, & 12, JNK, 5-LOX, Mcl-1, moesin, NPY, neurotensin, NF kappa B, PDK4, PGE2, substance P, surviving, tyrosine hydroxylase, VIP, vasopressin, VEGF levels and more.

Examples of adjunct agents include ACE inhibitors, captopril, elanapril and the like. Vitamin C (1000 mg 2-4×/day; P.O.), COX-2 inhibitors and/or omega-3 oils to decrease prostaglandin E2 synthesis, Vitamin D, Zn, Mg and Se to decrease NFk-β. Additionally, antibiotics include doxicycline, minocin, metronidazole and the like.

In certain embodiments, the following protocol or a similar one can be used:

1. treat with Amoxicillin or Doxycycline (100 mg/2×/day) or Minocycline (100 mg 2×/day) for 2 weeks; then 2. add azithromycin (250-500 mg 3×/week) or telithromycin (100 mg 2×/day) for 2 weeks plus Rifampin with or without isoniazid and an antiviral agent such as valtrex, valganciclovir and or a heparin deriviative; then 3. add metronidazole (500 mg 2×/day) for 5 days; then 4. two weeks off metronidazole (maintaining steps 1 & 2 above); then 5. pulse therapy with metronidazole (500 mg 2x/day) for 5 days on, 2 weeks off until symptoms of endotoxemia decrease; then 6. increase the dose of metronidazole to 1000 mg 2x/day or 2000 mg 2x/day until;

7. tumor cell death occurs, as measured via tumor specific markers appear in the appropriate compartment (e.g., blood, urine, etc); and 8. when tumor marker levels decrease to normal values, discontinue treatment.

In desperate scenarios that require aggressive treatment the immediate use of all agents simultaneously has been successful in eliminating HDS related disease (see Example with metastatic pancreatic cancer below): Amoxicillin (and/or NAC), doxycycline, azithromycin, Rifampin, metronidazole, Valtrex, curcumin, luteolin and iodine (Iodoral or equivalent). These agents can be used in conjunction with standard chemotherapy or radiation for neoplastic or autoimmune disease.

Adjuncts to this treatment include calcium channel blockers and EDTA, both of which disrupt persistent forms of pleomorphic organisms by reducing the availability of calcium.

Management of Endotoxemia

In certain embodiments, it can be desirable to supplement antibiotic therapy with treatments to decrease adverse effects of endotoxin. With the use of such adjunctive treatments, the doses of antibiotics may be increased to higher levels, or more rapidly, because the patient will be protected against at least some of the effects of endotoxin. These types of adjunctive therapies may be directed to one or more of several types of protection against endotoxin. These include:

1) Binding/Digesting Endotoxin to Prevent Recirculation and Accumulation:
   a. Charcoal 10-20 caps at 10 AM, 3 PM and 8 PM, optionally with acidophyssus;
   b. Cholestyramine Powder: I pack at 10 AM and one at 3 PM;
   c. High Fiber Diet: Steamed vegetables, brown rice, beans, salad;
   d. Enzymes: Lipram™ or Pangestyme™ or Ultrase or Creon having 20,000 USP of lipase per capsule to break down Lipid A in endotoxin. Can be administered with meals. Similase™ is an over-the-counter preparation: 5 capsules before meals.

2) Blocking NF kappa B & Angiotensin with ACE Inhibitors and Nutrition
   a. Zestril™ (lisinopril) 10-40-mg, increase gradually. ACE inhibitors reduce headache, anxiety, depression and appetite. Lowers NF kappa B activity, which controls inflammation;
   b. Quercetin™, 500 mg 2x/day. Found in Green Tea, slows growth of pancreatic cancer cells;
   c. Mg, 400 mg 2x/day;
   d. Zn, 30 mg daily;
   e. Se, 200 mcg daily.

3) Reduce endotoxin levels: Vitamin C: 500-100 mg 4x/day. Vitamin C drives Cpn into cryptic phase. Vitamin C lowers $PGE_2$ activity and increases apoliproprotein A1. Vitamin C needed for nitric oxide synthase, which can decrease pain. In animals that make Vitamin C, endotoxin stimulates Vitamin C. production. Because humans do not make Vitamin C, it must be ingested.

4) Decrease $PGE_2$:
   a. COX-2 Inhibitors. PGE2 is elevated in cancer and coronary artery disease.
   b. Omega-3 oils: 2-3 capsules/day, best in AM if DHA.
   c. Celebrex™ 200 mg/day or aspirin 325 mg/day.

5) Inhibit IL-6-Related Inflammation if Arthritis is Present. For example, use hydroxychloroquine (Plaquenil™); 200 mg ½ to 2x/day.

6) Liver Protection: Thistilyn™, 175 mg 3x/day.

7) Heparin lowers IFN-gamma and IDO reducing the activity of the kynurenin pathway, as well as possessing impressive antiviral properties.

8) Low Dose Naltrexone or other agents that inhibit the ability of HIT to stimulate opioid receptors.

Endotoxin increases $PGE_2$ levels. Inhibiting COX 2 decreases $PGE_2$ formation.

Adjunctive treatments can include agents that neutralize endotoxin (to decrease symptoms of endotoxemia), including plasmapheresis, intravenously administered alkaline phosphatase (e.g., calf-intestine alkaline phosphatase), endotoxin binding protein (EBP; Xoma, Berkeley Calif.), or 5-lipoxygenase inhibitors (e.g., Cingulaire™). Additional adjunctives can be used to decrease or prevent re-absorption of endotoxin from the gastrointestinal tract. Such agents include Questran™, cholestyramine, digestive enzymes (lipase, amylase, protease, e.g., Pangestyme™ or Lipram™; 20,000 U lipase equivalent) delivered 15 minutes before meals P.O. Additional adjunctives include Vitamin C, (at least 1000 mg 2-4x/day P.O. or intravenous), COX-2 inhibitors, Vitamin D, omega-3 oils, Zn, Mg and/or Se.

Endotoxin neutralizing agents include lipid A hydrolases: ESL04 and ES106 from CloneZyme Library, endotoxin binding protein: NEUPREX (rBPI21, opebacan) from Xoma, CIAP: Calf Intestine Alkaline Phosphatase from Biozyme (Blaenavon, UK), polymyxin B which binds endotoxin, agents which block prostaglandin synthesis=NSAIDs to mitigate early signs of endotoxemia, intravenous infusion or intramuscular dosing of immunoglobulin containing endotoxin binding antibodies (i.e.—Sandimmune or other forms of IVIG) and E5564, a synthetic lipid A analogue from Eisai Medical Research Inc., Teaneck, N.J., USA.

Treatment using the above protocol can continue until a tumor-specific marker indicates tumor cell death. For example, pancreatic cancer can be evaluated using CA 19-9, colon and breast cancers can be evaluated using CEA.

Additionally, endotoxin levels can be measured directly to determine the status of endotoxemia.

Adjunctive measures can also include the use of agents that increase levels of ACC, C1-esterase inhibitor, caspase (especially 8 & 10), caveolin-1, cystatin, cytochrome c oxidase, factor V, FADD, junB, melatonin, nitric oxide, orexin-A, oxytocin, PPAR gamma, TBG, and more. The neutralization LPS and the TLR4 signaling that initiates HDS, the elimination of the infectious agents or environmental sources of LPS, the maintenance of adequate ascorbic acid levels and other metabolic cofactors related to the inflammatory cascade (e.g., hormones, zinc, selenium, manganese, magnesium, vitamins A, B, D and E), has the potential of restoring health to those with HDS related illness by arousing patients from LPS induced dormancy.

Treatment of Cancer

Viral genes, called "oncogenes" are often associated with tumorogenesis. However, the immortalizing factor(s) for cancer cells have not been well understood. The known immortalizing (anti-apoptotic) factors include surviving, Bcl-2, and Bcl-xL which impart immunity to cancer cells rendering them invulnerable to chemotherapeutic agents such as cisplatin. Despite an exhaustive literature search we were surprised to find that these anti-apoptotic molecules, which we predicted are central to the survival of hibernating cells during the prolonged oxidative stress of hibernation, have not yet been investigated in the field hibernation research. These anti-apoptotic molecules are activated by LPS through binding with moesin, CD14 and TLR4. By interacting with moesin, CD14, and TRL4, LPS exploits a mechanism used by the host during in embryonic development and during hibernation or dormancy. It is during these periods that immune function is least protective to the host and body temperature decreases. Suppressing the host's body temperature (avoiding fever) during infection would favor bacterial and fungal survival. In that sense, we hypothesize that LPS has evolved as a bacterial and fungal strategy for survival, one that sends an artificial hibernation signal for the host's cells. The host is particularly vulnerable to infection during hibernation. Intracellular pathogens that release LPS and other superantigens that engage TLR4-mediated hibernation and embryonic mechanisms are among the most challenging to defend against.

Our surprising discovery, that the intracellular LPS-producing pathogen Cpn and other organisms are associated with immortalizing many if not most or all cancer cells is novel, and we are the first to demonstrate that anti-*Chlamydia pneumoniae* (anti-Cpn) treatment restores apoptosis to cancer cells and can lead to the spontaneous death of cancer cells. This is especially the case when high doses of metronidazole or other agents are employed to treat the anaerobic "cryptic" form of the organism.

According to one hypothesis, this new understanding is based on one or more of the following findings:
1.) Cpn is ubiquitous and most people are colonized with Cpn or related organisms.
2.) Cpn has an immortalizing effect on the host cells it infects (1).
3.) A low nitric oxide, low ascorbic acid, high oxidative stress (low GSH/GSSG ratio), high rT3/fT3 ratio, environment favors growth of LPS producing organisms, such as Cpn. People with Human Dormancy Syndrome have low nitric oxide levels, partially mediated by an elevated rT3/fT3 ratio as previously described in U.S. Pat. No. 7,288,257, incorporated herein fully by reference.
4.) Patents with fibromyalgia (FM) have low nitric oxide secondary to LPS induced Dormancy. Patients with FM have overgrowth of LPS producing organisms such as Cpn and FM remits with treatment that reverses Dormancy and eliminates LPS and the infectious organisms which produce LPS.
5.) Patients with FM have 50% greater risk of cancer mortality over a 10-year period than those without chronic pain associated with fibromyalgia (FM).
6.) Cpn infection promotes HDS with LPS which influences deiodinase activity, increasing rT3 levels which slows DNA transcription and metabolism in the same manner that placenta rT3 maintains dormancy during gestation.
7.) Elevated plasma and tissue levels of reverse T3 and rT3/fT3 ratio is a feature of many cancers and other Dormancy related conditions.
8.) Cpn infection is recognized as a causitive factor for T-cell lymphoma.

Thus, by eliminating LPS producing organisms such as Cpn from infected cancer cells, apoptosis can be restored and spontaneous apoptosis occurs leading to cancer cell death. Because dormancy favors Cpn growth in many ways and reversing dormancy, for example by raising body temperature to about 100° C. or more and optimizing rT3/fT3 ratio (e.g., by administering T3), favors the elimination of Cpn. Reduced body temperature of no more than 4 degrees is observed in polar bears that are in a state of dormancy referred to as "Walking Hibernation." Body temperature for human beings who have triggered HDS and the related disease states is on average, 97.3 degrees orally, but is often lower, especially during periods of increased stress. Temperatures as low as 95.4° C. have been observed in patients with HDS.

Although fever is normally a feature of disseminated infection, it is not a feature of infection in hibernating animals, nor is it common in subjects having chronic infection with LPS producing atypical organisms such as Cpn. Engaging the host's dormancy response by increasing rT3 levels and inhibiting NOS activity with IL-6, or depleting ascorbic acid levels following prolonged LPS-related oxidative stress, which further impairs immunity can be an adaptive survival strategy for Cpn. Lower body temperature and lower nitric oxide levels can impair WBC function, and these changes can occur when an animal's dormancy or hibernation shift is engaged. Cpn has developed the ability to exploit the host's dormancy defense through the release of LPS, which can increase HSP-60 and HSP-70, especially in ascorbic acid deficient hosts, and can directly impairing mitochondrial function of cells that are involved in mitigating Dormancy. For example, hibernating squirrels have recently been found to cycle out of hibernation every 7 days, presumably to enhance immune function. During the arousal period, a period of high oxidative stress, squirrel ascorbic acid levels increase dramatically. Dormancy that is associated with Cpn-related LPS may not allow for periods of elevated body temperature as seen in uninfected hibernating animals. Arousal from Dormancy may be further inhibited by depletion of ascorbic acid in hosts that lack an endogenous source since increased production of ascorbic acid is a feature of arousal. HDS related conditions are frequently associated with ascorbic acid depletion, as well as abnormal levels of ascorbic acid related metabolites; these abnormalities appear to further impair the host's ability to end Dormancy and are frequently associated pathological processes.

While most DNA mutations do not lead to apoptosis, cells infected with organisms that chronically trigger TLR's are forced to immortalize (suspended apoptosis) which can lead to cancer with ot without DNA mutation. Elimination of the immortalizing signals (LPS and other TLR stimulating superantigens) that trigger dormancy and embryonic cellular metabolism, restores apoptosis to these cells, leading to spontaneous apoptosis and death of cancer cells. This is especially true of intracellular LPS and HSP producing organisms such as Cpn, especially the cryptic phase of the organism.

Until now, the DNA mutations were assumed to be the sole source of cancer cell immortalization. This assumption would require that all tumor cells have mutations that influence apoptosis, a type of cell death that is associated with caspase synthesis. Since mutations do not always include this system, this explanation is at best, incomplete. Based on our unexpected findings, LPS-related immortalization through Cpn is associated with the ability to immortalize any cell it inhabits, which may apply to a variety of cancer cells. This relationship is supported by the examples described herein of cancer cell apoptosis following comprehensive treatment of Cpn infections in human beings suffering from cancer.

There is little histologic similarity between adenoid cystic carcinoma, colon cancer, and pancreatic cancer. In spite of this apparent heterogeneity, anti-LPS with anti-Cpn treatment lead to aoptosis of each of tumor types. This approach to therapy is effective for a variety of histologically unrelated tumor cells. This supports the concept that LPS-induced HDS, probably through intracellular infection with Cpn, is a potential source for the immortalization of cancer. The ubiquitous nature of Cpn, its use of LPS, and our unexpectedly broad results supports this hypothesis. Cancer can then be redefined as a condition that may or may not be associated with a DNA mutation in an LPS-triggered, hibernating, embryonically-shifted, proliferating cell that is frequently Cpn infected. Our novel approach to cancer treatment focuses on restoring apoptosis to cells that are influenced by LPS-producing organisms, especially intracellular organisms such as Cpn, by neutralizing LPS and eliminating the HDS-perpetuating organism. The presence of the fetal protein moesin in gestation, hibernation, cancer, autoimmune disease, and following LPS exposure supports this relationship. The finding of elevated alpha-fetoprotein, and carcinoembryonic antigen levels in gestation, cancer, and in conjunction with LPS exposure further supports the mechanism of HDS and its sequellae. High doses of metronidazole may be necessary to eliminate the cryptic phase of Cpn and this treatment can desirably be given in conjunction with other antibiotics, including those that block the extracellular and replication intracellular forms of Cpn along with additional signals that support the arousal from hibernation.

Treatment of Autoimmune Diseases

Autoimmune diseases are depicted as a group of diseases involving the immune system in a dysregulated manner to produce an inflammatory process that is ultimately destructive to the body. These diseases may involve all tissues: skin, subcutaneous fat, ligament, muscle, joint, nerve, artery, vein and viscera. The source of these diseases is largely not known. Those who suffer from these diseases are believed to have an underlying genetic predisposition that is triggered by unknown environmental factors. It is believed by some that once the triggering event has occurred, immune dysregulation follows. Some researchers have suggested that it is molecular mimicry that leads to perpetuation of the immunologic reaction in the absence of the original environmental trigger. For example, most patients who develop reactive arthritis after food poisoning with *salmonella* ingestion have HLA B-27 white blood cell (WBC) surface antigens that predispose them to inappropriate immune response to *salmonella*. More specifically, a theory proposes that surface proteins from *salmonella* may induce an antibody and T-cell response that cross reacts with joint tissue in those who develop reactive arthritis.

One theory holds that similarities between the host's cells and the *salmonella* cells leads to self-attack (autoimmune disease) by the immune system which continues to attack the host's cells after the *salmonella* cells are eliminated. The theory of molecular mimicry is frequently used to explain conditions where chronic infections cannot be documented as a source of ongoing immune system activity. Autoimmune conditions, such as systemic lupus erythematosus (SLE), have been studied in identical twins who carry identical genetic and immunologic markers for the disease, and yet, the concordance of SLE between identical twins is less than 10%, leading researchers to believe that SLE is caused by a combination of genetic predisposition and environmental triggering from sources that are not currently understood. SLE has been triggered in association with the hormonal changes of pregnancy, emotional and physical trauma, and a number of infections. Once triggered, SLE is considered an autoimmune process that is not driven by an infection, but instead the disease is considered an overactive immune system that is best treated with immunosuppressants. Hashimoto's thyroiditis is another autoimmune condition believed to be caused by antithyroperoxidase antibody production (antibodies that attack thyroid tissue) and lymphocytic infiltration into the thyroid gland, gradually destroying the thyroid cells. Hashimoto's thyroiditis is commonly seen in patients with SLE, although a common mechanism for the two autoimmune diseases does not currently exist. A cure for Hashimoto's thyroiditis does not exist, and the disease is currently allowed to run its natural course to hypothyroidism followed by thyroid hormone supplementation. The current invention proposes a common mechanism for autoimmune conditions as well as novel treatment that is directed at the underlying source of "autoimmune" reactions.

Autoimmune diseases can be exacerbated by emotional and physical stress. Barometric change is sometimes sufficient to trigger a flare-up of rheumatoid arthritis. This phenomena is well-recognized, but the mechanism is not currently understood. This invention provides a mechanism that explains the influences of stress on these diseases and will lead to novel treat approaches for the previously mentioned features of autoimmune disease.

Stress (which includes emotional and physical trauma, infection and inflammation) increases oxidative processes and places a demand on the organism to respond. A biphasic response is frequently observed with acute stress temporarily increasing fT3 levels and reducing rT3 levels for as long as 2 hours in some experimental settings, followed by a decrease in fT3 production, which decreases nitric oxide production; a feature of human dormancy syndrome. Although this response reduces unnecessary loss of body heat and diminishes the need for calories when the stress is cold environmental temperature, this response is maladaptive for most other sources of stress. Nitric oxide is essential for WBC's to combat bacteria and other pathogens. Persons with low nitric oxide levels would be at increased risk of developing infections from commonly encountered organisms that exploit those with low nitric oxide levels.

Processes that activate moesin, CD14, and TLR4 create an environment that favors the growth of organisms that rely on LPS for survival. Chronic exposure to environmental sources of LPS may predispose a host to HDS and increase the risk of bacterial or fungal overgrowth with LPS producing organisms. For example, dried tobacco leaves are high in endotoxin, presumably from mold LPS that accumulates during the drying process. Inhalation of LPS laden smoke promotes localized changes in the lung that favors the growth of LPS producing organisms in those tissues. The LPS related infection would further promote localized HDS-related changes in lung tissue, promoting cancer, an HDS-related sequellae. The detrimental effects of LPS appears to be exacerbated by depletion of ascorbic acid, which is depleted by tobacco smoke and is low in patients with lung cancer. Ascorbic acid has a 30-minute half life, making it especially vulnerable to depletion during prolonged exposure to oxidative stress. LPS producing infections exploit these physiologic opportunities.

*Chlamydia pneumoniae* is such an infection. This commonly encountered organism usually infects through the respiratory route and is able to evade destruction from WBC's in a number of ways, including the use of amphiphysin IIm, a vacuole protein coating that allows this organism to live within, and parasitize macrophages and monocytes, impairing their ability to function properly. Once the organism resides within the WBC's, it is able to disseminate throughout the body to other tissues and cells where is impairs their function. This infection is difficult to diagnose because blood tests for obligate intracellular organisms are commonly false negative. This infection is difficult to treat because curative treatment appears to require that multiple antibiotics be given simultaneously for many months (similar to tuberculosis). Tissue culture for this organism requires special cell cultures that are not often available in commercial settings which further complicates the recognition of *Chlamydia pneumoniae* infection in those with autoimmune disease. Stress lowers nitric oxide and ascorbic acid levels, which allows *Chlamydia pneumoniae* to flourish. Infection causes the release of inflammatory mediators that further decreases free T3 and nitric oxide production as described in the human dormancy syndrome, specifically through the effect of inflammatory cytokines on 5' D2 and iNOS activity. Immunologic stimulation triggered directly by the *Chlamydia pneumoniae* antigens can produce vasculitis, arthritis, and other autoimmune features. However, once macrophage function has been impaired by *Chlamydia pneumoniae* infection, the host is made more susceptible to other infectious agents.

In the case of SLE patients, they are susceptible to multiple bacterial infections, including *Neisseria* species and viral infections. What has not been considered is the potential for colonized fungal infections to induce autoimmune disease by providing a constant source of antigenic material for the immune system to contend with. Secondly, immuno-compromised macrophages can allow colonized fungi to disseminate. Fungal culture of the sinus mucosa renders positive cultures for 2-3 different species of fungus in virtually all people. What is different for those with chronic airway disease from those who are asymptomatic is that those with rhinosinusitis have eosinophil activation. Tissue biopsies from symptomatic patients show eosinophic infiltration and elevations in eosinophilic cationic protein levels. These findings are typically present in asthma patients as well as in patients with rhinosinusitis, suggesting the process of fungal mucosal colonization likely extends to the bronchial mucosa. This has led the hypothesis that asthma and rhinosinusitis are one disease and that fungal colonization with eosinophilic activation to fungus is involved in both disease processes.

What had not been explained is why some people become symptomatic with sensitized eosinophils and why others tolerate the colonization. Aspects of this invention are based upon the finding that a drop in nitric oxide production allows *Chlamydia pneumoniae* to disseminate and infect mucosa and macrophages, both of which will impair the host's capacity to control mucosal fungal infection by shifting their metabolic pattern to that of HDS. Other infectious agents, including mycoplasma and more typical bacterial infections, may play a role in asthma and COPD, but the unique nature of *Chlamydia pneumoniae* to live within and compromise macrophages and monocytes makes this infectious agent of central importance. The difficulty in detecting the presence of this organism contributes to the misconception that the diseases it is associated with are autoimmune rather than infectious.

With respect to Hashimoto's thyroiditis, it is possible that the lymphocytic infiltration of the gland is in response to infection of the thyroid gland by virus, fungus and/or bacteria. For example, fungi possess mitochondria, and mitochondrial function is enhanced by T3. Fungi DNA have T3 receptors, and this makes the thyroid gland a likely target for fungal colonization. Colonization of the thyroid gland by fungus will lead to immunologic activity against the gland. Just as colonization of the intestine with *salmonella* and exposure of the WBC's to *salmonella* proteins can induce arthritis, it is likely that the many species of mold that colonize human mucosa can serve as a source of antigens for immune activation. Over 40 species of colonizing mold have been cultured at the Mayo Clinic, and these fungal proteins have thus far not been investigated as a source for autoimmune diseases.

Thus, there is a connection between HDS, viral infection, *Chlamydia pneumoniae*, and fungal colonization with eosiophilic activation and low-grade systemic fungal infection and processes that are currently considered to be autoimmune. Both *Chlamydia pneumoniae* and airborne fungal spores are ubiquitous, and it is likely that all people are exposed to and colonize these organisms. A competent immune system would likely prevent overgrowth or dissemination of these mucosal colonies. However, stress that is sufficient to trigger human dormancy syndrome will decrease fT3 levels that will lower nitric oxide production that will favor dissemination of *Chlamydia pneumoniae*. Once macrophage function is impaired, additional growth of colonized fungus is likely. The fungal antigens drive immunologic reactions that include vasculitic reactions and type 3 hypersensitivity reactions such as serum sickness as well as the expected type 1-hypersensitivity reactions referred to as atopy. The use of antifungal medication alone is unlikely to be curative when concomitant *Chlamydia pneumoniae* infection and HDS are present and macrophage impairment is ongoing. The same is true of viral infection in that all TLR stimulating infections can desirably be adequately addressed to reverse the metabolic shift into HDS.

The current approach to diagnosis and treatment of autoimmune disease involves a careful history and physical examination followed by confirmatory laboratory tests such anti-CCP antibodies, RF, ANA, ASM, AMA, and anti-dsDNA antibodies, along with C3, C4, urinalysis, CBC and imaging studies where indicated. Once the autoimmune process is identified and the severity of the process is determined, graded immunosuppressive therapy is instituted. The current trend in immunosuppressive treatment has been influenced by the devastating disability that is common when the chronic inflammatory process is not sufficiently suppressed. The current standard of care is to provide aggressive suppression at an earlier stage of the disease than was offered ten years ago.

In view of the relationships that have been described with respect to the biochemistry of dormancy, nitric oxide levels, viral infection, *Chlamydia pneumoniae* and other atypical bacterial infection and fungal colonization with eosinophil activation, this invention contemplates a new paradigm for the treatment of autoimmune disease. The history and physical exam should include investigation for known signs and symptoms of human dormancy syndrome, atypical bacterial, viral and fungal infection. Serologic evaluation should seek to document the presence of exposure to atypical bacteria, virus and fungal infection, and culture or DNA or other antigen assays should be considered. The rT3/fT3 ratio can assess the degree of shifting toward dormancy and guide the clinician in their assessment of the potential need for treatment of the dormancy component of the illness. Ascertaining systemic and/or local nitric oxide levels will also be of benefit. Serum, plasma or tissue levels of endotoxin (LPS), NF kappa B, angiotensin, kinin, moesin, CD14, activated TLR4, apolipoprotein A1, Bcl-2, Bcl-xL, surviving, CGRP, c-jun, junB, and many other features of embryonic or hibernation related metabolism can help assess the degree of HDS and potential for HDS related sequellae. Measurement of tumor markers and autoimmune markers are also helpful for the purpose of assessing HDS. Physical exam findings of fibromyalgia and tender point tenderness correlates with a reduction in endogenous nitric oxide production. In addition to the standard proven techniques for controlling the life-threatening features of autoimmune disease, measures should be taken to treat dormancy, atypical bacterial, virus and fungal infections, as these are components of autoimmune disease. Since fungus growth is stimulated by T3, the inclusion of antifungal medication, either topical or systemic, should be considered when reversing dormancy with T3 therapy. Prophylactic antifungal treatment, and antiviral treatment may be helpful when long-term antibiotic therapy is instituted for atypical bacterial infection.

Following diagnosis, the initial approach to treatment is to decrease LPS and related superantigens as well as block the pathways that are exploited by LPS and related superantigens. It is the signal from the superantigens, rather than the presence of infection that is most harmful to the host. Initial treatment should include LPS neutralizing agents that bind or dephosphorylate LPS rendering it inactive. Oral supplementation with digestive enzymes (including lipase and alkaline phosphatase) can neutralize the component of LPS released from the liver into the bowel with biliary secretions. Plasmapheresis or IVIG for LPS release may also be helpful during aggressive treatment of HDS related bacterial or fungal overgrowth. The normalization of key enzymes and cofactors in LPS related pathways are also an important consideration. For example, NF kappa B activity is elevated in cancer, autoimmune disease, infection, hibernation and gestation. NF kappa B activity is further enhanced by deficiencies in selenium, zinc, magnesium, vitamin D and ascorbic acid, hence these cofactors must be addressed and remain replete during treatment of HDS related conditions.

The use of ACE inhibitors to decrease NF kappa B activity and normalize ACE activity, and lower the elevated angiotensin and kinin levels during treatment facilitates recovery. This is especially important when treating cancer since angiotensin increases the release of Bcl-2 and Bcl-xL, both of which confer immortality on cancer cells. COX-2 activity is elevated in HDS as is the cancer promoting end product of COX-2 metabolism, PGE2. The use of omega 3 oils and ascorbic acid lower COX-2 activity and PGE2 production. The use of NSAID's, especially COX-2 inhibitors is also helpful for HDS related diseases by normalizing another HDS related pathway. 5-LOX activity is elevated in HDS diseases and the use of ascorbic acid and/or 5-LOX blocking agents such as Singulair, reduce leukotriene production and normalize another HDS related pathway. Since the levels of ascorbic acid achievable through oral supplementation are significantly lower than those achievable through IV administration of ascorbic acid, the temporary use of IV ascorbic acid during intensive therapy may be a helpful adjunct in the treatment of HDS related conditions. The intent is to create an environment, with respect to ascorbic acid in this instance, that reflects what is observed in animals arousing from hibernation.

Other measures designed to enhance endogenous nitric oxide production should be considered and these include, but are not limited to, aspirin, oxytocin, arginine or MSM. The treatment of Chlamydia pneumoniae infection can require a prolonged period of therapy, including anti-porphyric measures. Calcium channel blockers, which have been shown to enhance the effectiveness of antibiotics against Chlamydia pneumoniae by preventing the calcium influx that is necessary for Cpn to remain in the cryptic phase of it's life cycle, may be used in conjunction with antibiotics for patients with Chlamydia pneumoniae related autoimmune disorders. Vitamin C has been recently shown to impact Cpn infected macrophages in vitro, driving the organism into cryptic phase. An important therapeutic application of this invention is gene therapy using adeno-associated virus or other suitable vectors to introduce the gene for L-gulonolactone oxidase into the human genome. It is the omission of this enzyme that is responsible for our inability to synthesize ascorbic acid. Restoration of ascorbic acid synthesis would optimize our ability to respond constructively to oxidative stress by allowing for increased synthesis of ascorbic acid and it's metabolites in response to LPS stimulation. The treatment of fungal colonization may include topical antifungal nasal spray and nebulized antifungal solutions or inhaled aerosolized antifungal liquids or powders to reduce the burden of fungus growth at these sites, while systemic antifungal medication is necessary for the treatment of disseminated fungal infections, including Hashimoto's (fungal) thyroiditis. Thyroid needle biopsy may be necessary for diagnostic purposes to obtain tissue confirmation using either bacterial/fungal DNA assays or culture of both for Chlamydia pneumoniae and/or fungus. These diagnostic techniques and treatments are not currently applied to autoimmune disease processes, and this approach represents an advance toward palliative and/or curative treatment for autoimmune disease. More effective treatments for Chlamydia pneumoniae and fungal infections, as well as the development of new medications to prevent dormancy-related physiologic changes, as described in U.S. patent application Ser. No. 10/444,845, incorporated fully by reference, are also beneficial to patients with autoimmune disease. Table 4 shows relationships between fibromyalgia, traumatic stress disorder and dormancy.

TABLE 4

FM, Post Traumatic Stress Disorder and Dormancy

| Variable | FM | PTSD | DORMANCY |
|---|---|---|---|
| Slow Wave Sleep Impaired | Yes | Yes | Yes |
| Irritable Bowel (IBS) | Yes, low VIP | Yes | Yes, low VIP |
| HPA Dysregulation | Yes | Yes | Yes |
| High CRH | Yes | Yes | Yes |
| Sympathetic Hyperactivity | Yes | Yes | Yes |
| CSF Substance P | Increased | Increased | Yes |
| Pain Perception | Increased | Increased | ? |
| Serotonin | Low | Low | Yes |
| Prolactin | Increased | Increased | Increased |
| Growth Hormone Response | Blunted | Blunted | Yes |
| Oxytocin | Low | Low | Yes |
| Nitric Oxide Metab Abnormal | Yes | Yes | Yes |
| Cerebral Blood Flow | Centralized | Centralized | Yes |
| Cognitive Function | Impaired | Impaired | Yes |
| Orthostatic Hypotension | Yes | Yes | ? |
| Fatigue | Yes | Yes | Yes |
| Exercise Intolerance | Yes | Yes | Yes |
| Mitochondrial Impairment | Yes | Yes | Yes |
| Hypervigilance | Yes | Yes | Yes |
| Compulsivity | Yes | Yes | ? |
| Detachment/Dissociation | Yes | Yes | ? |
| Depression/Anxiety | Increased | Increased | ? |
| Significant Emotional Trauma | Yes | Yes | N/A |
| Impaired NK Cell Activity | Yes | Yes | Yes |

Embodiments of this invention include measurement of endotoxin and related bacterial and fungal surface superantigens, NF kappa B activity, ACE activity, CD14 levels, moesin levels, Bcl-2 or Bcl-xL levels, Chlamydia pneumoniae and/or fungus antibodies, or direct culture of these organisms or testing of antigens, immune complexes or DNA from these organisms. Thus, in certain aspects of this invention, the treatment of human dormancy syndrome, Chlamydia pneumoniae and/or fungus can be beneficial for treating underlying causes of autoimmune diseases.

Aspects of this invention are based on the new observation that several medical conditions, including cancer and autoimmune disorders heretofore unassociated with each other have a common etiology: HDS, with secondary infection by Chlamydia pneumoniae and/or fungus.

In addition to Chlamydia, Mycobacterial infections are desirably treated. Although there are no currently available commercial tests for Mycobacterium, treating an underlying infectin by this organism can be useful. In particular, antibiotics such as isoniazid, rifampin, Rifabutin or ethambutol can be useful.

Measurement of organisms that have the capacity to initiate and maintain HDS through use of moesin, CD14 or TLR pathways, as well as viruses that increase interferon gamma (IFN-gamma) which directly increases IDO activity. Testing for any infectious agent that increase quinolinic acid production (kynurenine pathway end product). These organisms include but are not limited to those that can reside intracellularly, especially those that exist within macrophages. These organisms have the capacity to initiate HDS with HSP:

M. avium-intracellulare, M. kansasii, M. xenopi, M. malmoense, M. fortuitum, M. chelonei M. ulcerans, M. marinum, M. tuberculi, M. paratuberculosis, M. pneumoniae,
B. burgdoreri, B. garini, B. henselae
T. whipelli
C. pneumoniae, C. psitaci, C. trachomatis and
S. typhi.

When treatment of HDS addresses one or more of the above infections using antibiotics, JH reactions can occur, followed by substantial improvements in function. In two patients, treatment with antibiotics that address the above organisms resulted in improvement. In one patient, grip strength doubled after treatment.

Viral coinfection is common when macrophages are infected by intracellular pathogenic bacteria, and testing of these viral infections for assessing or treating HDS related sequellae is considered to be part of this invention. Such viruses include, by way for example only, HHV6, HHV7, EBV, CMV, HIV, HPV-B19, Herpes Zoster, HSV1, HSV2, Simian Virus.

Fungal organisms make potent antigens that stimulate TLR pathways, especially Th2 pathways and therefore their overgrowth contributes to HDS. Testing by PCR or other means for these organisms has potential for detecting perpetuating factors for HDS. Such fungi include, by way of example, *Aspergillus, Penicillium, Candida, Alternaria, Cladosporium*, and *Mucor*.

Compositions for Treatment of Cancer

Based on the descriptions above and the Examples below, additional aspects of this invention include compositions of agents useful for treating cancer. In general, these compositions include at least one antimicrobial and one anti-HDS agent in a physiologically acceptable medium. However, it is apparent that one can use multiple antimicrobials and multiple anti-HDS agents in a composition.

In certain embodiments, an antimicrobial can be one or more of INH, minocin, azithromycin, metronidazole, amoxicillin, rifampin, ethambutol and acyclovir. Anti-HDS agents can be one or more of luteolin, curcumin, niacinamide or ascorbic acid. These compounds can be formulated in physiological media, including saline, phosphate-buffered saline, and may include any needed surfactants, oils and the like for administration.

Compositions containing antimicrobial and anti-HDS compounds may be administered using oral, nasal, buccal, intravenous, subcutaneous, intramuscular or other route. For injection, the compounds included should be sterilized before use. However, for oral administration, compositions should be free of orally infections agents. Because many of the anti-HDS agents are not regulated drugs, and may be purchased commercially, one only need to use the usual precautions for ingestion of these compounds.

EXAMPLES

The examples that follow are intended to illustrate aspects of the invention and are not intended to limit the scope of the invention.

Example 1

Killing of Fibroblasts In Vitro

In a series of studies under supervision of the Inventor carried out at Stanford Research Institues (SRI), 3T3 fibroblasts were grown in culture and exposed to combinations of antibiotics with and without added anti HDS agents. Table 5 shows the conditions of the studies.

TABLE 5

Conditions for Fibroblast Study In Vitro

| Solution A | Target Concentration ug/mL | vial 1 mg | vial 2 mg | DMSO | 0.1N NaOH in water | Growth Media | Phosphate Buffer |
|---|---|---|---|---|---|---|---|
| Minocin | 20 | 20 | 21 | 2 grams | none | 96 grams | 2 grams |
| Azithromycin | 0.4 | 1 | 1 | | | | |
| Metronidazole | 35 | 35 | 35 | | | | |
| Amoxicillin | 7.5 | 7.5 | 7.5 | | | | |
| Acyclovir | 4 | 4 | 4 | | | | |
| Total weight | 66.9 | 67.5 | 68.5 | | | | |

| Solution B | Target Concentration ug/mL | vial 3 mg | vial 4 mg | DMSO | 0.1N NaOH in water | Growth Media | Phosphate Buffer |
|---|---|---|---|---|---|---|---|
| Luteolin | 42 | 42 | 42 | 2 grams | 8 grams | 88 grams | 2 grams |
| Curcumin | 5 | 5 | 5 | | | | |
| Niacinamide | 50 | 50 | 54 | | | | |
| Ascorbic Acid | 100 | 100 | 116 | | | | |
| | 197 | 197 | 217 | | | | |

| Solution C | ug/mL | vial 5 mg | vial 6 mg | DMSO | 0.1N NaOH in water | Growth Media | Phosphate Buffer |
|---|---|---|---|---|---|---|---|
| Minocin | 20 | 20 | 20 | 2 grams | 8 grams | 88 grams | 2 grams |

TABLE 5-continued

Conditions for Fibroblast Study In Vitro

| | | | |
|---|---|---|---|
| Azithromycin | 0.4 | 1 | 1 |
| Metronidazole | 35 | 35 | 36 |
| Amoxicillin | 7.5 | 7.5 | 7.5 |
| Luteolin | 42 | 42 | 42 |
| Curcumin | 5 | 5 | 5 |
| Niacinamide | 50 | 57 | 52 |
| Ascorbic Acid | 100 | 100 | 100 |
| Acyclovir | 4 | 4 | 4 |
| | 263.9 | 271.5 | 267.5 |

Results

FIG. 1 is a graph depicting results of studies in 3T3 fibroblasts. Composition A (Solution A in the above Table 6; mixture of 5 antibiotics) showed little effect alone. Surprisingly, composition B (Solution B; containing luteolin, curcumin, niacinamide and ascorbic acid) inhibited cell growth substantially in a concentration-dependent fashion with a maximum of nearly 100% inhibition at the highest dose tested. Further addition of antibiotics (Composition C; Solution C) had no additional effect. Thus, we conclude that 3T3 fibroblasts are relatively insensitive to antibiotics but are quite sensitive to anti HDS agents. This finding was totally unexpected based on previous studies of fibroblast cell growth.

The relative lack of effect of antibiotics in these cells is not surprising in that these calls are not known to harbor intracellular pathogens. The 3T3 fibroblasts are non-cancerous. However, they are abnormal in that they are immortalized. We unexpectedly found that the anti HDS agents "mortalized" these cells, thereby limiting their ability to survive in cell culture. There is no evidence to support the possibility that any of the agents in Composition B used independently are toxic in these doses to normal fibroblasts. However, it was totally unexpected to find that the anti HDS agents were so effective at inhibiting fibroblast cell growth. This finding was totally unexpected based on the known properties of 3T3 fibroblasts.

Example 2

Killing of Human Pancreatic Cancer Cells In Vitro

In another study to determine the effects of the above compositions in human cancer, we carried out a series of studies supervised by the Inventor and carried out at SRI using Capan-1 Human Pancreatic Cells (C-1 HPC) in vitro.

Experimental Procedure

Preparation of Test Solutions

The test article will be a mixture of 8 different compounds. The solubility of each individual compound was provided. For testing the mixture, appropriate amount of each individual compound was weighed out and dissolved in proper solvent. A portion of each individual solution was mixed to produce a stock solution of that mixture. The stock solutions were diluted with cell culture medium to produce different concentrations of the mixture. The mixtures consisted of group A, group B and group C, with group C being a combination of A & B together. The solutions were tested at two concentrations, one at full strength and another at 50% concentration. In addition to testing the mixtures with cancer cell cultures, the solutions were tested with non-cancerous cells as controls to ensure that the mixture's apoptotic effect was specific to cancer cells.

Cell Proliferation Assay

Human Capan-1 pancreatic cancer cells (C-1 HPC) were maintained in RPMI-1640 medium supplemented with 10% fetal bovine serum at 37° C. in an atmosphere of 95% air/5% $CO_2$ and 100% humidity. When cells reach 80% confluence, they were harvested using a 0.25% trypsin/EDTA solution. The harvested cells were reseeded in 96-well plates at a density of 2,000 cells/well in 200 µl of medium. Cells were allowed to attach for 24 h, then various concentrations of the test compound were added to each appropriate well. Vehicle without test compound was added to control wells. Four wells were used for vehicle control and each drug concentration. Cells were incubated for 6 days and medium was replaced on Day 3 with fresh test solutions added. At the end of 6 days, viable cells were measured by the MTT assay.

The MTT assay (Promega Corporation, Madison, Wis.) was conducted by removing a 100 µl aliquot of medium from each well and replace that aliquot with 100 µl fresh medium and followed by adding 15 µL of tetrazolium dye solution. The cells were then incubated for additional 4 h. During the 4 h of incubation, viable cells converted the tetrazolium salt to a formazan product which produced a blue color. Following the 4 hour incubation period, 100 µL of Solubilization/Stop solution was added to each well. The plate was kept overnight at room temperature and the blue color of the product was measured at a wavelength of 575 nm using an ELISA plate reader. The absorbance was plotted against each concentration and an $IC_{50}$ value will be derived from the curve.

Subsequently, based on the $IC_{50}$ values, appropriate concentrations of each agent were selected to produce a detectable but not large degree of inhibition when administered alone. Thus, any synergistic effect between agents could be detected.

C-1 HPC were derived from a patient having pancreatic cancer. It is well recognized that studies of human cancer cells in vitro are reasonably predictive of human cancers in vivo. Further, studies of inhibition of cancer cell growth in vitro are reasonably predictive of anti-cancer effects observed in human beings in vivo.

Results

Figure 2:
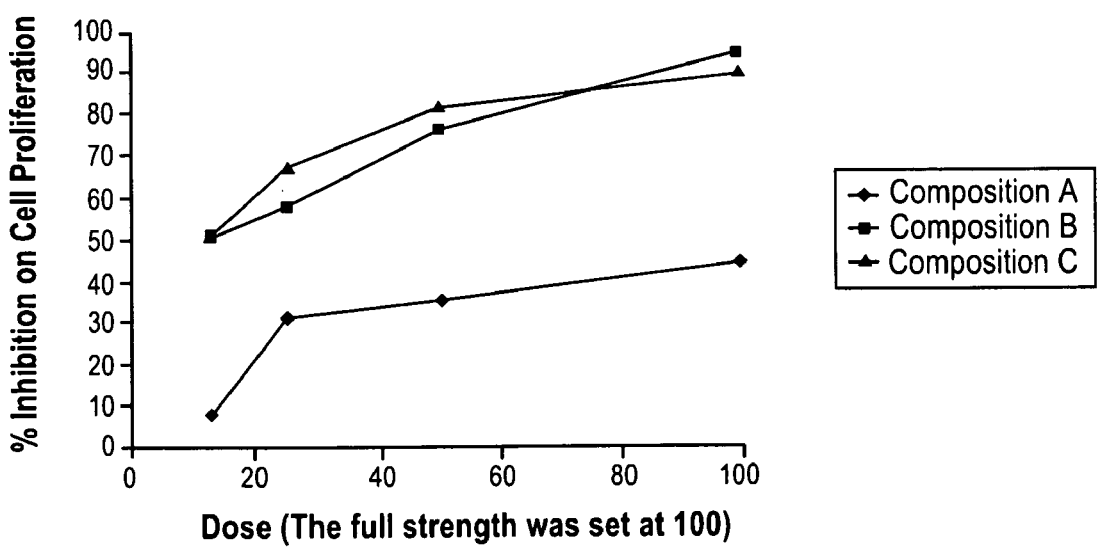
FIG. 2 depicts a graph of dose of compositions of this invention versus % inhibition of growth of Capan-1 human pancreatic cancer cells.

FIG. 2 is a graph depicting results of studies using the Compositions A, B and C described above in Example 1.

Composition A alone inhibited growth of C-1HPCs in vitro in a concentration dependent fashion, with a maximal effect observed at 100% of the full strength dose. Thus, we conclude that C-1HPC cells are highly likely to harbor intracellular organisms that are sensitive to the antibiotics used. This finding was totally unexpected based on the traditional view of cancer and tumorogenisis.

Composition B (Solution B) substantially inhibited growth of C-1HPC in vitro, with a maximal effect of nearly 95% inhibition at the highest dose tested. Further addition of antibiotics had little additional effect. This effect was totally unexpected based on the known properties of cancer and tumorogenesis.

It is well known that pancreatic cancer is one of the most difficult tumors to treat. Life expectancy may be as little as 3-6 months after diagnosis. With the advent of this new approach, pancreatic cancer and other types of cancer with traditionally poor outcomes may now be teatable using compositions of this invention.

We conclude from this Example, that anti-HDS agents, luteolin, curcumin, niacinaminde and ascorbic acid provide an important new and unexpected potent treatment of human pancreatic cancer cells in vitro. We also conclude that these agents can produce nearly complete killing of the cancer cells. Because of the well-known use of in vitro cell culture methods for identifying potentially useful therapeutic agents, these results are reasonably predictive of the therapeutic effects that will be observed in vivo and support use of these agents in treatment of patients suffering from pancreatic cancer. Of significance is that none of the agents in Solution B (Composition B) studied here are known to have toxic side effects. They are all available without prescription.

Example 3

Treatment of Pancreatic Cancer in a Patient

A patient presents with a diagnosis of pancreatic cancer. After clinical evaluation and confirmation of the diagnosis, the patient is placed on a treatment protocol as follows:
1. The following agents are administered concurrently:
   a. Curcumin: 1000-1200 mg 3×/day;
   b. Vitamin C: 500 mg 3×/day;
   c. Niacinamide: 1500 mg/2×/day, increasing to 2,000 mg/2×/day and then, if necessary to 3,000 mg 2×/day;
   d. Luteolin: ¼ tsp-½ tsp 2-3 times in the AM.
2. Subsequently, and if desired, the above protocol is maintained, to which misoprostol is added at a dose starting at 200 microgram tabs; ½ 2×/day and then increasing to 1 tab 4×/day as tolerated.
3. If desired, antichalydial therapy is initiated using metronidazole 1 gm 2×/day, increasing to 2-4 gm 2×/day as tolerated.
4. If desired, ursodiol (in capsule form) is administered at a dose of 300 mg 2-3×/day. Alternatively, Ursoforte™ is available in 500 mg tablets and can be substituted for the capsule form.

Therapy is maintained until improvement in symptoms is observed.

Example 4

Case Report: Successful Treatment of Metastatic Pancreatic Cancer

A 53 year old female diagnosed with metastatic pancreatic cancer involving her liver presented for treatment in October of 2006. Her oncologist could not offer her curative treatment but advised her that a course of gemzar, oxaliplatin, and Tarceva might extend her life by 3 months. Her life expectancy was 3-6 months and her initial tumor marker CA19-9 level was elevated at 626.3 Units/mL (negative<39) in Oct. 5, 2006 at our first meeting. She was found to have a variety of positive serologies for infectious agents that have the capacity to suspend apoptosis. She consented to treatment with a combination of amoxicillin, rifampin, azithromycin, metronidazole, Valtrex, curcumin, luteolin, ursodiol, pangestyme, assorted vitamins and iodine. She was encouraged by us to take the chemotherapy her oncologist recommended while she received the above antimicrobial and anti-hibernation treatments.

Eight months later she was pancreatic cancer-free as determined by PET scan, MRI, and the minimally suspicious region in her liver (PET negative) was biopsied and found to be non-cancerous. Her CA19-9 was 48 U/ml in January 2007, 9 U/ml in July 2007, and 5 U/ml in November 2007. She stopped Oxaliplatin in May 2007, and stopped Tarveca in June. Antimicrobials were discontinued in July, but treatment with anti-hibernation agents continued and continues to be well tolerated. She has no detectable trace of pancreatic cancer and has remained in this state of good health for greater than half a year at the time of this writing. The best available chemotherapy for pancreatic cancer will extend life an average of 3 months. This case demonstrates the therapeutic potential of treating infection mediated HDS related cancer in this manner.

This Example and Example 2 therefore demonstrate that antimicrobials and anti-HDS compounds are effective in killing pancreatic cancer cells in vitro and for successfully treating metastatic pancreatic cancer in vivo. This strategy of treating infection and HDS is a useful method for cancer therapy in human beings.

Example 5

Killing Human Breast Cancer Cells In Vitro I

In another study, we determined the effects of anti-bacterial and anti-hibernation therapy on human breast cancer cells in vitro. The studies were carried out at Stanford Reasearch Institue (SRI) under the direction of the Inventor. AU565 human breast cancer cells are known to express high levels of the breast cancer antigen HER2. In vitro studies of treatments for human cancer, including breast cancer, are well recognized in the art as being reasonably predictive of effects of those treatments in vivo. Thus, observing efficacy in retarding growth of cancer cells in vitro is reasonably predictive of an expected therapeutic effect in vivo.

Experimental Procedure

Test Mixtures

The test compositions were mixtures of different components from 4 groups of drugs, namely, A, B, C, and D. There were a total of 11 mixtures tested. The 11 mixtures were: (1) mixture B, (2) first component of B labeled as B1, (3) second component of B labeled as B2, (4) third component of B labeled as B3, (5) fourth component of B labeled as B4, (6) mixture A, (7) first component of A labeled as A1, (8) second component of A labeled as A2, (9) third component of A labeled as A3, (10) mixture C, and (11) mixture D. All the mixtures were provided as pre-mixed samples and ready for testing. The experminenter did not know which components were present in any test mixture.

Cell Proliferation Assay

Human CRL-2351 breast cancer cells were maintained in RPMI-1640 medium supplemented with 10% fetal bovine serum at 37° C. in an atmosphere of 95% air/5% $CO_2$ and 100% humidity. When cells reached 80% confluence, they were harvested using a 0.25% trypsin/EDTA solution. The harvested cells were reseeded in 96-well plates at a density of 2,000 cells/well in 200 µl of medium. Cells were allowed to attach for 24 h, then various concentrations of the test compounds were added to each appropriate well. Vehicle without test compound was added to control wells. Four wells were used for vehicle controls and at each drug concentration. Cells were incubated for 6 days and medium was replaced on Day 3 with fresh test solutions added. At the end of 6 days, viable cells were measured by MTT assay.

The MTT assay (Promega Corporation, Madison, Wis.) was conducted as described above in Example 2.

Plates of cells were grown in growth medium in the presence of solutions of 2-deoxyglucose (4100 µg/ml) and etomoxir (90 µg/ml) containing compounds shown below. Solutions 1, 2 and 3 include antibiotics. Solutions 4, 5, 6, 7, 8, 10 and 11 contain anti-hibernation compounds. Solution 9 is a combination of antibiotics and anti-hibernation compounds. Table 6 below shows the conditions of this study.

TABLE 6

Test Conditions for Breast Cancer Study In Vitro

| | Target Concentration (µg/ml; 100%) | Code |
|---|---|---|
| Solution 1 | | IREMMA-1 |
| INH | 5 | |
| Rifampin | 9 | |
| Ethambutol | 5 | |
| Minocin | 20 | |
| Metronidazole | 35 | |
| Acyclovir | 4 | |
| Solution 2 | | IREMMA-2 |
| INH | 5 | |
| Rifampin | 9 | |
| Ethambutol | 5 | |
| Minocin | 20 | |
| Metronidazole | 60 | |
| Acyclovir | 4 | |
| Solution 3 | | IREMMA-3 |
| INH | 5 | |
| Rifampin | 9 | |
| Ethambutol | 5 | |
| Minocin | 20 | |
| Metronidazole | 35 | |
| Acyclovir | 4 | |
| Telithromycin | 2.3 | |
| Solution 4 | | LCNC-4 |
| Luteolin | 42 | |
| Curcumin | 5 | |
| Niacinamide | 50 | |
| Ascorbic acid | 100 | |
| Solution 5 | | Luteolin@42 |
| Luteolin | 42 | |
| Solution 6 | | Curcumin@5 |
| Curcumin | 5 | |
| Solution 7 | | Niacinamide@50 |
| Niacinamide | 50 | |
| Solution 8 | | C@100 |
| Ascorbic acid | 100 | |
| Solution 9 | | IREMMAKLCNC-9 |
| INH | 5 | |
| Rifampin | 9 | |
| Ethambutol | 5 | |
| Minocin | 20 | |
| Metronidazole | 35 | |
| Acyclovir | 4 | |
| Telithromycin | 2.3 | |
| Leuteolin | 42 | |
| Curcumin | 5 | |
| Niacinamide | 50 | |
| Ascorbic acid | 100 | |
| Solution 10 | | Ursodiol@15 |
| Ursodiol | 15 | |
| Solution 11 | | Misoprostola@1 |
| Misoprostol | 1 | |

Results

Figure 3:
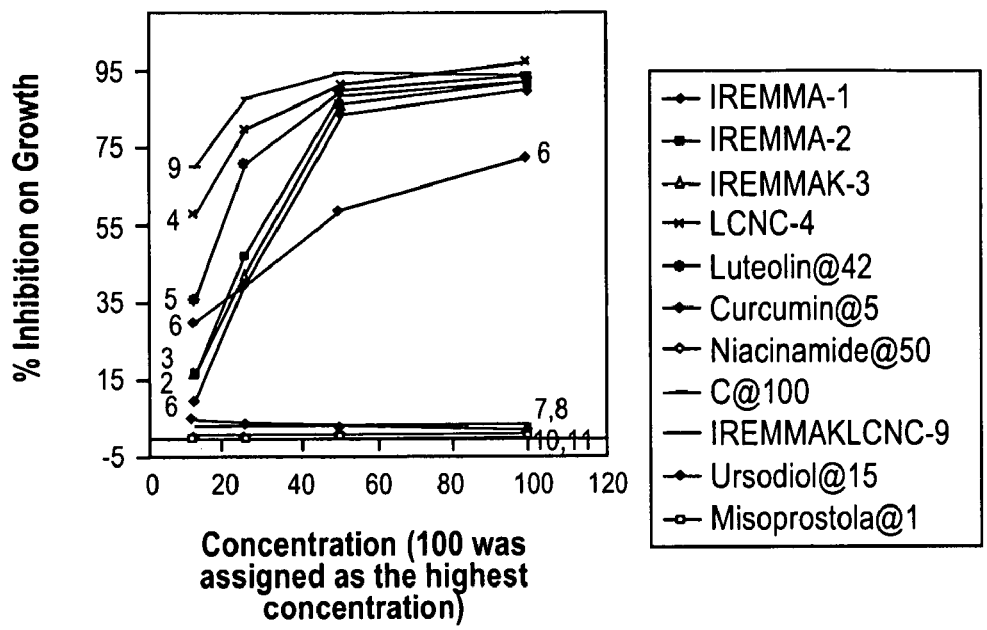
FIG. 3 depicts a graph of doses of compositions of this invention versius % inhibition of AU565 human breast cancer cells with high expression of the antibody HER2.

FIG. 3 depicts results of the studies. We unexpectedly found that at low doses, antibiotics alone produced a modest inhibition of cancer cell growth (about 15% to about 30%). We also found that anti-hibernation compounds inhibited cancer cell growth in a concentration-dependent fashion, with an effect at the lowest concentrations of from about 10% to about 60%. Thus, even at low concentrations, anti-hibernation compounds substantially inhibited cancer cell growth. We unexpectedly found that the combination of antimicrobial agents plus anti-hibernation compounds increased the level of inhibition of cell growth. At the lowest concentrations, solution 9 inhibited cancer cell growth by about 70%. Increasing the concentrations of the compounds further inhibited cancer cell growth, with 90-95% inhibition at the half-maximal dose used.

Example 6

Killing Human Breast Cancer Cells In Vitro II

To determine if a combination of antimicrobial agents plus anti-hibernation agents would act synergistically to inhibit cancer, we carried out another study with the human breast cancer cell line AU565 in vitro. We used solution #3 as described above, which included isoniazid (INH), rifampin, ethambutol, minocycline, metronidazole, acyclovir and telithromycin at a 2% concentration of the previous mixture used in Example 5. This was to decrease the cell growth inhibition to ease interpretation of the results. We combined #3 with #6 (curcumin) and #3 with #5 (luteolin) to investigate the synergistic potential of these combinations using the following procedure. The experimenter did not know what the compositions were at the time of the experiment.

Experimental Methods

Cell Culture

AU565 human breast cancer cells were routinely maintained in RPMI-1640 medium supplemented with 10% fetal bovine serum, 2 mM sodium pyruvate, and 4.2 g/L glucose. The cells were cultured at 37° C. in an atmosphere of 95% air/5% $CO_2$ and 100% humidity. When cells reached 80% confluence, they were harvested using 0.25% trypsin/EDTA solution. The harvested cells were re-suspended in appropriate medium and reseeded in 96-well plate at a density of 3,000 cells/well/200 µl. Cells were allowed to attach for 24 h, then various concentrations of the test compositions were added to each appropriate well. Vehicle without test compositions were added to control wells. Four wells were used for vehicle control and each composition concentration. Cells were incubated for 6 days and medium was replaced on Day 3 with fresh test solutions added. At the end of 6 days, viable cells were measured by MTT assay as described above in Example 2.

Combination Study

From the $IC_{50}$ values of all the compositions tested, 3 potent compositions were selected for a combination study. The 3 compositions were labeled as #3, #5, and #6. In this combination study, a 2% solution of #3, 4% of #5 and 12.5% of #6 were tested alone or in combination of 2 or 3 compositions together in mixtures. When mixing 2 or 3 compositions together, an appropriate concentration of each individual composition was mixed so that the final concentration in the assay would be 2%, 4%, and 12.5% for compositions #3, #5, and #6 respectively.

Results

The results are as follows and are expressed as percent inhibition of tumor cell growth:
Sample #3 alone (2%): 32% inhibition
Sample #6 alone (12.5%): 9% inhibition
Sample #5 alone (4%): 10% inhibition
Sample #3 (2%)+sample #6 (12.5%): 55% inhibition
Sample #3 (2%)+sample #5 (4%): 62% inhibition
Sample #3 (2%)+sample #6 (12.5%)+sample #5 (4%): 64% inhibition.

Figure 4:
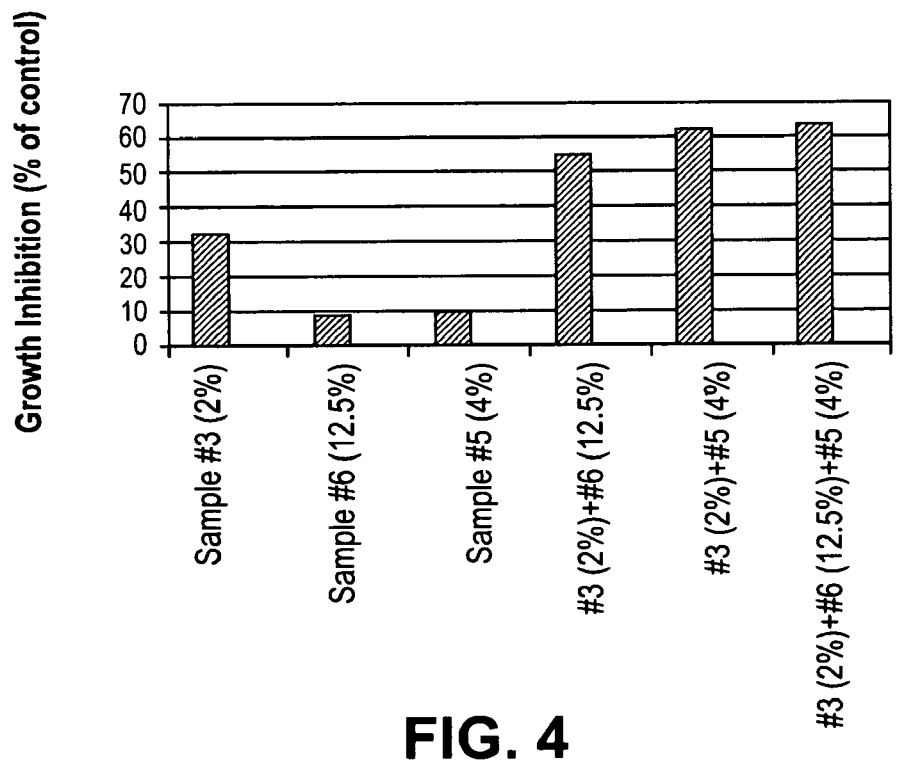
FIG. 4 depicts a graph showing results of studies of compositions of this invention versius % inhibition of AU565 human breast cancer cells with high expression of the antibody HER2. This study shows unexpected synergy between antimicrobial treatment and anti-hibernation treatment, leading to unexpectedly high tumor cell killing.

The above results are shown in FIG. 4.

It can be readily appreciated that the inhibition in tumor cell growth caused by sample #3+sample #6 (antimicrobials+luteolin) of 55% is greater than the sum of the individual effects (32%+9%=41%). The greater effect of the combination was totally unexpected based on the effects of the individual components.

Similarly, it can be appreciated that the inhibition in tumor cell growth caused by sample #3+sample #6 (antimicrobials+curcumin) of 62% was greater than the sum of the individual effects (32%+10%=42%). The greater effect of the combination was totally unexpected based on the effects of the individual components.

We conclude from this study that growth of human breast cancer cells can be substantially inhibited by anti-hibernation compounds and that this effect is increased by antimicrobials in a synergistic and unexpected fashion. We further conclude that because all of the compounds tested are suitable for human use, combinations of anti-hibernation and antimicrobials are suitable for human therapy. Furthermore, we conclude that because human cancer cells in vitro are an art recognized system reasonably predictive of human cancer growth in vivo, that use of anti-hibernation compounds and antimicrobials are reasonably effective in treating human patients with breast cancer.

We also conclude that luteolin or curcumin can be useful for inhibiting HDS-related phenomena, and that in combination with antimicrobial agents, luteolin and curcumin can act in a synergistic fashion to kill cancer cells. Thus, these orally available, non-prescription anti-HDS compounds can be useful in treating cancers.

Adjunct Therapies

In addition to the therapeutic approaches disclosed herein above, one can appreciate that conventional anti-cancer therapies can also be used, either before, during or after treatment as described. Chemotherapy, radiation therapy, and/or surgery can be used in conventional ways. For example, a first approach to treating a localized, non-metastatic tumor could be surgical excision. In situations in which surgery is insufficient, localized radiation therapy can be used. In situations in which neither surgery nor localized radiation therapy alone is sufficient, chemotherapy can also be considered.

Thus, this invention provides new and potentially useful additional modes of therapy for treating heretofore difficult to treat disorders. By treating underlying microbial infections and HDS, the body can be stimulated to return to its normal, non-dormant condition, improve defenses to disease, can prolong and improve the quality of life for many patients suffering from cancer.

Specialty Clinics

The approach to medicine described herein is novel. As of today, there are no facilities that provide comprehensive treatment for HDS and the sequellae. This invention includes specialty clinics designed to employ the techniques described herein to reverse HDS and its sequellae. The personnel in these clinics will approach HDS-related conditions with the knowledge that LPS producing organisms drive the syndrome by signaling the host to alter it's cellular functions with activation of TLR4 through LPS and other superantigens that create dormancy familiar to all humans in utero, a state that is not different from hibernation in larger animals.

Neutralization of LPS, and the use of specific cofactors to reverse trends seen in chronic conditions such as cancer and autoimmune disease are necessary to arouse cells from dormancy. The use of medication to purposefully block pathways that are activated by LPS, such as ACE inhibitors and ARB's, COX-2 inhibitors, 5-LOX inhibitors and more are helpful to arouse cells from dormancy. Elimination of LPS producing infections is also an important feature of the treatment of HDS related conditions.

Testing of endotoxin, NF kappa B, angiotensin, kinin, HIT levels or the rT3/fT3 ratio are not currently employed in the standard practice of medicine, and these tests along with assays for LPS producing organisms will be used in the specialty clinic setting for the treatment of HDS related conditions. The possible use of adeno-associated virus gene therapy to restore endogenous GLO synthesis to treat or prevent HDS related illness would also fall under the domain of the specialty clinic. Creation of CD14 or moesin blocking agents to prevent endotoxin from signaling TLR4 and other dormancy related receptors can also be seen as therapy designed for the reversal of HDS. Facilities using any part of this invention for the purposes of treating HDS or HDS-related illness by reversing dormancy or neutralizing endotoxin without proper authorization and licensing will be considered to be infringing upon this invention. Health insurance companies that support the use this technology for their insured or providers without authorization and licensing from the owners of this technology are infringing upon this invention.

CONCLUSIONS

The studies described above demonstrate that numerous cancers can be effectively treated using a combination of antimicrobial agents and anti-HDS agents together. These agents act in a synergistic fashion to increase the observed cell killing to levels substantially greater than the sum of the individual effects. These studies also demonstrate that combination therapy using antimicrobial agents and anti-HDS agents can have strikingly large effects, with some studies showing greater than 95% cell killing. These effects are totally unexpected based on either prior art therapies or on the observed effects of the agents individually.

The studies also show that the effects of antimicrobial agents and anti-HDS agents are not limited to a single or even two types of cancers. Effective cell killing was observed in two types of breast cancer cells and a pancreatic cancer cell line. Additionally, combination therapy was shown to be effective in treating human metastatic pancreatic cancer, with a surprisingly good outcome, with the patent living well beyond the expected few months from diagnosis.

The studies are also genelalizable to other forms of cancer and cells showing deviant growth patterns. Immortalized fibroblasts also are sensitive to anti-HDS agents, with those cells' growth slowed substantially by anti-HDS agents. Even though fibroblasts are not cancer, their unusual growth (immortalization) in vitro is characteristic of cancerous cells.

In conclusion, the methods disclosed herein provide new understanding of and new tools for treatment of cancers. The new understanding is based on the unexpectedly successful treatment of cancers using combinations of antimicrobial agents and anti-HDS agents. The approaches of this invention can permit successful cancer therapy without relying exclusively upon surgery, radiation therapy, chemotherapy or other currently available approaches. In fact, in patients who have had surgery that did not remove all of the tumor, or those who have received their maximal lifetime exposure to radiation, or who have not found chemotherapy successful or tolerable can have additional options for treating their cancers.

This invention has been described with reference to specific embodiments thereof. Other variations of the methods described herein can be made by persons of ordinary skill in the therapeutic arts without undue experimentation. All of those variations are considered to be part of this invention. All references cited herein are incorporated fully by reference in their entirety.

I claim:

1. A method for treating cancer in a patient, comprising the steps of:
   (a) identifying a patient susceptible to therapy, said patient diagnosed with:
      (i) breast or pancreatic cancer; and
      (ii) human dormancy syndrome (HDS) wherein the diagnosis of the HDS includes a finding of a serum ratio of reverse triiodothyronine to free triiodothyronine (rT3/fT3) of greater than about 4;
   (b) administering at least one first antimicrobial agent; and
   (c) administering luteolin, curcumin, niacinamide and ascorbic acid.

2. The method of claim 1, wherein said diagnosis of HDS further includes:
   a) one or more further findings selected from the group consisting of elevated levels of fungal or bacterial DNA, *Chlamydia, Mycoplasma, Mycobacteria*, Herpes virus, fungal serology, alpha 2-macroglobulin, alpha-fetoprotein, angiotensin II, Bcl-2, Bcl-XL c-fos, c-jun, ACE activity, CGRP, calsequestrin, CEA, catalase cathespin B, cholesterol, LDL, cIAP-2, connexin 43, CRF, COX-2 activity, d-dimer, endothelin-1, endotoxin, enkephalin, epithelial growth factor, FADD, fas ligand, fas/APO 1 ratio, FLIP, gastrin, ghrelin, glutathione peroxidase, FABP, heme oxygenase-1, hormone-sensitive lipase, HSP70, HIF-1, HIT, ICAM-1, IGF-1, IL-6, JNK, kallikrein, kinin, lipoxygenase, MAPK, Mcl-1, neuropeptide Y, neurotensin, NF kappa B, pancreatic triglyceride lipase, PDK, peptide YY, prolactin, prostcyclin, PGE2, protein kinase C, resistin, rT3, serine protease, substance P, superoxide dismutatse, survivin, TNF alpha, tyrosine hydroxylase, UCP2 and 3 activity, VIP, vasopressin, and VEGF, or
   (b) one or more findings selected from the group consisting of decreased levels of alpha-1 antitrypsin, antithrombin III, apolipoprotein, ascorbic acid, Bax, Bid, Bad, C1-esterase inhibitor, caspase, caveolin-1, cystatin, cytochrome-c oxidase, dopamine, Factor V, fT3, glyceraldehyde-3-phosphate dehydrogenase activity, GSH/GSSG ratio, IGFBP, junB, melatonin, Na/K ATPase activity, nitric oxide, orexin-A, hypocretin-1, oxytocin, p53, PARP, PPAR gamma, ROCK-2, secretin, serotonin, and TRAIL activity.

3. The method of claim 1, further comprising administering an iodine-containing compound so that the ratio of serum rT3/fT3 decreases to below about 4.

4. The method of claim 1, wherein said patient has an elevated titer of one or more from the group consisting of a viral antibody, viral DNA, viral RNA, fungus, *Chlamydia pneumoniae; Chlamydia pneumoniae* DNA, immunofluorescent stain for fungus in the thyroid gland, and immunofluorescent stain for *Chlamydia pneumoniae* in the thyroid gland.

5. The method of claim 1, wherein said at least one first antimicrobial agent is selected from the group consisting of amoxicillin, azithromycin, isoniazid, rifampin, doxycycline, valacyclovir, valgancyclovir and metronidazole.

6. The method of claim 5, comprising administering a second antimicrobial agent.

7. The method of claim 1, wherein said step of administering includes further administering a compound is selected from the group consisting of potassium iodide, naltrexone, naloxone, heparin, and hydroxychloroquine.

8. The method of claim 1, wherein said step of administering said at least one antimicrobial agent comprises:
   (a) administering 100 mg/2×/day of either amoxicillin or doxycycline or minocin for 2 weeks; then
   (b) along with the antibiotic of step (a), administering 250-500 mg 3×/week azithromycin or 100 mg 2×/day telithromycin for 2 weeks; then
   (c) administering 500 mg 2×/day metronidazole for 5 days; then
   (d) ceasing treatment with metronidazole for two weeks while maintaining steps (a) & (b) above); then
   (e) administering 500 mg 2×/day metronidazole for 5 days on, 2 weeks off until symptoms of endotoxemia decrease; then
   (f) administering metronidazole at a dose of 1000 mg 2×/day or 2000 mg 2×/day until tumor cell death occurs.

9. The method of claim 1, further comprising administering one or more agents to reduce adverse effects of endotoxin selected from the group consisting of an endotoxin binding agent, ursodiol, an endotoxin neutralizing agent, an agent to inhibit NF kappa B activity, an agent to inhibit ACE, Vitamin C, Vitamin B12, an agent to inhibit cyclooxygenase-2 (COX-2), an omega-3 oil, an agent to inhibit interleukin-6 (IL-6), an agent to inhibit a toll-like receptor (TLR), an agent to inhibit metalloproteinase activity and an agent to protect the liver from endotoxin damage.

10. The method of claim 1, further comprising a therapy selected from the group consisting of chemotherapy, radiation therapy and surgical therapy.

11. The method of claim 1, further comprising administration of one or more second antimicrobial agents selected from the group consisting of amoxicillin, azithromycin, isoniazid, rifampin, doxycycline, valacyclovir, valgancyclovir and metronidazole.

* * * * *